United States Patent
Perryman et al.

(10) Patent No.: US 9,717,921 B2
(45) Date of Patent: Aug. 1, 2017

(54) TREATING INFLAMMATION, CHRONIC PAIN AND OTHER DISORDERS WITH NEUROMODULATION

(71) Applicants: Laura Tyler Perryman, Miami Beach, FL (US); Chad Andresen, Miami Beach, FL (US)

(72) Inventors: Laura Tyler Perryman, Miami Beach, FL (US); Chad Andresen, Miami Beach, FL (US)

(73) Assignee: Micron Devices, LLC, Miami Beach, FL (US)

(*) Notice: Subject to any disclaimer, the term of this patent is extended or adjusted under 35 U.S.C. 154(b) by 0 days.

(21) Appl. No.: 14/775,218

(22) PCT Filed: Mar. 14, 2014

(86) PCT No.: PCT/US2014/029704
§ 371 (c)(1),
(2) Date: Sep. 11, 2015

(87) PCT Pub. No.: WO2014/153223
PCT Pub. Date: Sep. 25, 2014

(65) Prior Publication Data
US 2016/0015988 A1    Jan. 21, 2016

Related U.S. Application Data

(63) Continuation-in-part of application No. PCT/US2013/073326, filed on Dec. 5, 2013, and a
(Continued)

(51) Int. Cl.
*A61N 1/378* (2006.01)
*A61N 1/36* (2006.01)
(Continued)

(52) U.S. Cl.
CPC ............ *A61N 1/3787* (2013.01); *A61B 34/20* (2016.02); *A61N 1/36071* (2013.01);
(Continued)

(58) Field of Classification Search
CPC ...... A61N 1/0551; A61N 1/3605; A61N 1/05; A61N 1/3787; A61N 1/36071;
(Continued)

(56) References Cited

U.S. PATENT DOCUMENTS

| 6,941,171 B2 * | 9/2005 | Mann ................ A61N 1/36007 128/898 |
| 2002/0055761 A1 | 5/2002 | Mann et al. |

(Continued)

OTHER PUBLICATIONS

Authorized Officer Shane Thomas, International Search Report and Written Opinion in PCT/US2014/029704 mailed Aug. 21, 2014, 20 pages.

*Primary Examiner* — Deborah Malamud
(74) *Attorney, Agent, or Firm* — Fish & Richardson P.C.

(57) ABSTRACT

Some implementations provide a method of treating chronic pain or inflammation with neural modulation, the method including: placing a surgical instrument to reach into a torso section of a patient's body, the patient suffering from chronic pain or inflammation in a primary area in the torso section; placing a wireless device into an opening on the surgical instrument, the wireless device suitable to fit into the opening and configured to receive electromagnetic energy non-inductively from a source located outside the patient's body; through the opening on the surgical instrument, positioning the wireless electrode lead adjacent to or near excitable tissue in the primary area in the torso section of the patient; and causing electrical pulses to be delivered to one or more electrodes on the wireless device such that neural modulation is applied to the excitable tissue in the primary area in the torso section.

22 Claims, 32 Drawing Sheets

Related U.S. Application Data continuation-in-part of application No. 13/551,050, filed on Jul. 17, 2012, now Pat. No. 9,409,030, and a continuation-in-part of application No. 13/562,221, filed on Jul. 30, 2012, now Pat. No. 9,199,089, and a continuation-in-part of application No. 13/584,618, filed on Aug. 13, 2012, now Pat. No. 8,849,412, and a continuation-in-part of application No. 13/621,530, filed on Sep. 17, 2012, now Pat. No. 9,242,103, and a continuation-in-part of application No. 14/045,764, filed on Oct. 3, 2013, now Pat. No. 9,220,897.

(60) Provisional application No. 61/786,049, filed on Mar. 14, 2013.

(51) Int. Cl.
*A61N 1/372* (2006.01)
*A61B 34/20* (2016.01)
*A61B 1/313* (2006.01)
*A61B 90/00* (2016.01)

(52) U.S. Cl.
CPC ..... *A61N 1/37205* (2013.01); *A61N 1/37229* (2013.01); *A61B 1/3132* (2013.01); *A61B 2090/376* (2016.02); *A61B 2090/378* (2016.02)

(58) Field of Classification Search
CPC .. A61N 1/36017; A61N 1/37235; A61N 1/36; A61N 1/36021; A61N 1/3752; A61N 1/36125; A61N 1/36146; A61N 1/3758; A61N 1/04; A61N 1/08; A61N 1/0472; A61N 1/3606; A61N 1/372; A61N 1/375; A61N 1/3968; A61B 5/05; A61B 5/4836; A61B 18/1482; A61B 1/018; A61B 1/3132; A61B 5/40; A61B 5/686; A61B 5/6887; Y10S 439/909; H01B 7/048; D10B 2509/00

See application file for complete search history.

(56) References Cited

U.S. PATENT DOCUMENTS

| | | |
|---|---|---|
| 2006/0149337 A1 | 7/2006 | John |
| 2008/0213331 A1 | 9/2008 | Gelfand et al. |
| 2011/0015695 A1 | 1/2011 | Pasricha et al. |
| 2011/0106208 A1 | 5/2011 | Faltys et al. |
| 2011/0106219 A1 | 5/2011 | Cauller et al. |
| 2012/0283800 A1 | 11/2012 | Perryman et al. |

\* cited by examiner

Lead/Receiver 704
(anchored to heart wall)

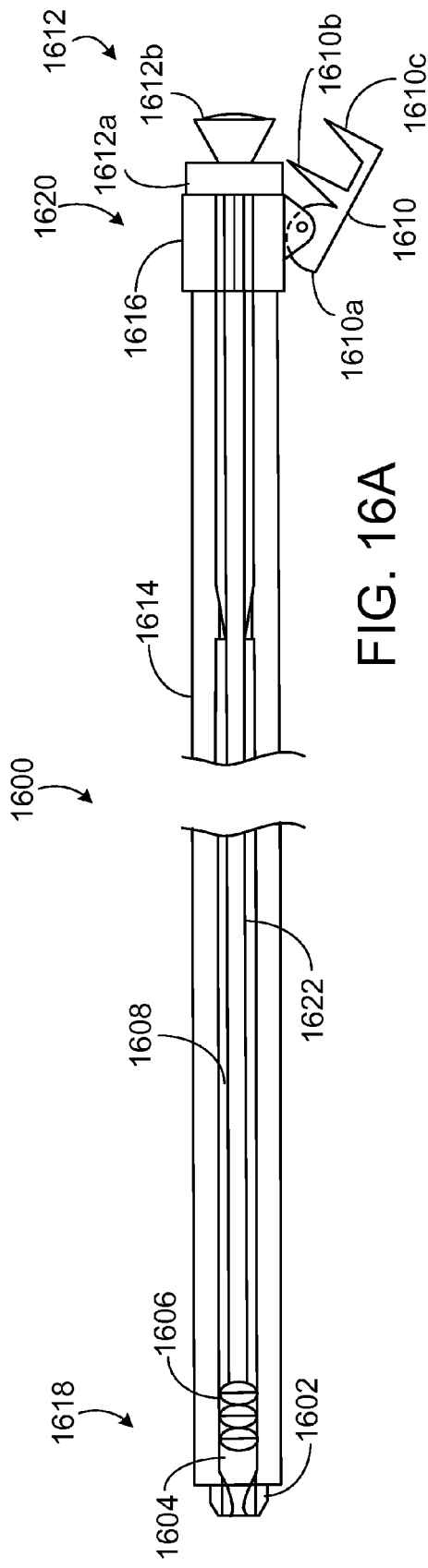
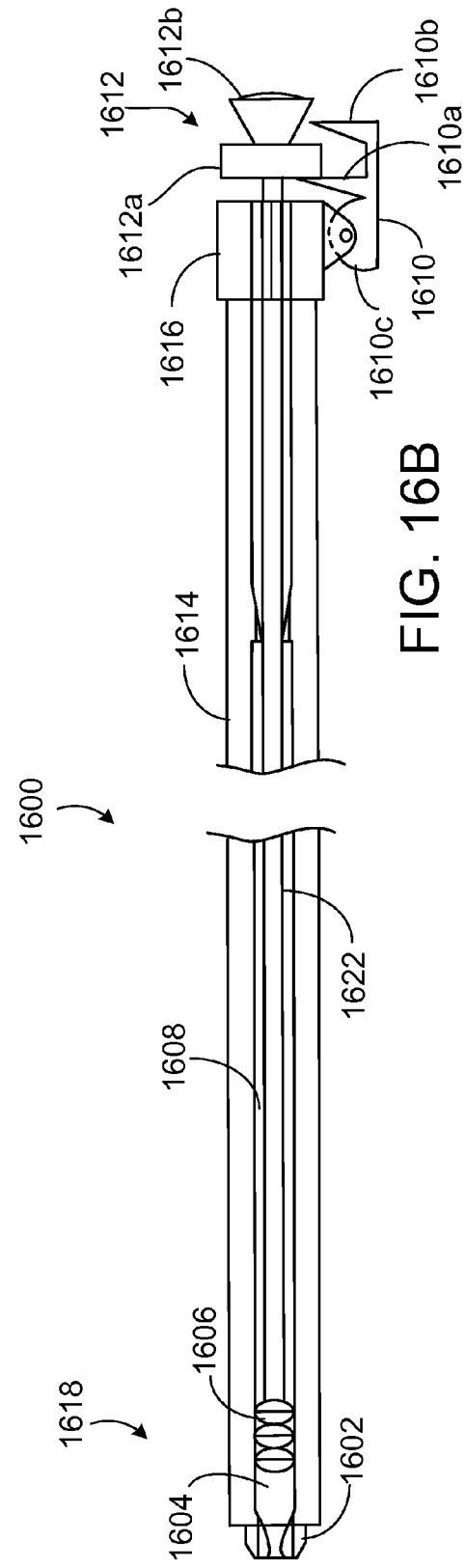

TREATING INFLAMMATION, CHRONIC PAIN AND OTHER DISORDERS WITH NEUROMODULATION

CROSS REFERENCE TO RELATED APPLICATIONS

This application claims benefit of U.S. provisional Patent Application 61/786,098, filed Mar. 14, 2013. Under 35 U.S.C. 365 and 120, this application claims the benefit of and is a continuation in part of PCT application PCT/US2013/073326, filed Dec. 5, 2013, U.S. patent application Ser. No. 13/551,050 filed Jul. 17, 2012, U.S. patent application Ser. No. 14/045,764 filed Oct. 3, 2013, U.S. patent application Ser. No. 13/562,221, filed Jul. 30, 2012, U.S. patent application Ser. No. 13/584,618, filed Aug. 13, 2012 and U.S. patent application Ser. No. 13/621,530, filed Sep. 17, 2012. The disclosures of all of these applications are incorporated by reference in their entirety for all purposes.

TECHNICAL FIELD

The present application relates to the delivery of energy impulses (and/or fields) to excitable tissues for therapeutic purposes.

BACKGROUND

Modulation of excitable tissue in the body by electrical stimulation has become an important type of therapy for patients with chronic disabling conditions, including chronic pain, pain associated with cancer, incontinence, problems of movement initiation and control, involuntary movements, vascular insufficiency, heart arrhythmias, obesity, diabetes, craniofacial pain and more. A variety of therapeutic intrabody electrical stimulation techniques can treat these conditions. Typically, such devices utilize a subcutaneous battery operated implantable pulse generator (IPG) to provide power or other charge storage mechanisms.

SUMMARY

In one aspect, a system for treating a variety of disorders, inflammation and/or chronic pain comprises one or more devices that have electrodes configured to apply one or more electrical impulses to excitable tissue, particularly nerves associated with pain, inflammation or disorders in the digestive track, heart, pancreas, spleen, kidneys and the like. The electrical impulses are sufficient to modulate the nerves to treat pain, inflammation and/or digestive disorders. The devices are coupled to a power supply and pulse generator for generating the electrical impulses.

In some implementations, the power supply and pulse generator are not directly attached to the device. Some implementations may use wireless devices that include a first antenna coupled for receiving an input signal from a second antenna, remote from the first antenna. The second antenna may be external to the patient's body or it may be positioned on the patient's body or implanted within the patient's body remotely from the first antenna. The power supply and pulse generator may be directly connected to the second antenna, or they may be physically separate from the second antenna. In this latter example, a relay remote antenna may be used to transmit the input signal from the pulse generator to the second antenna.

In some implementations, the second antenna is configured to transmit an input signal. The input signal may include power and may define the electrical pulses for driving the electrodes. The first antenna is configured to receive the input signal non-inductively and without a wired connection. Electronic circuitry may be coupled to the first antenna and may extract the electrical power and electrical pulses from the input signal. The electronic circuitry may then send the electrical pulses to one or more electrodes. The one or more electrodes may modulate the targeted nerves using the electrical pulses. In one example, the one or more electrodes and the antenna are housed within an enclosure of the wireless device. The enclosure may be configured for subcutaneous placement on the patient's body or percutaneous placement within the patient's body.

In one aspect, some implementations provide a method of treating chronic pain or inflammation with neural modulation, the method including: placing a surgical instrument to reach into a torso section of a patient's body, the patient suffering from chronic pain or inflammation in a primary area in the torso section; placing a wireless device into an opening on the surgical instrument, the wireless device suitable to fit into the opening and configured to receive electromagnetic energy non-inductively from a source located outside the patient's body; through the opening on the surgical instrument, positioning the wireless electrode lead adjacent to or near excitable tissue in the primary area in the torso section of the patient; and causing electrical pulses to be delivered to one or more electrodes on the wireless device such that neural modulation is applied to the excitable tissue in the primary area in the torso section.

Implementations may include one or more of the following features. Placing the surgical instrument may include positioning a laparoscopic device into an abdominal region of the patient's body. Placing a wireless device into an opening on the surgical instrument may include placing the wireless device through a working channel or cannula of the laparoscopic device. Positioning the wireless device adjacent to or near excitable tissue may include positioning the wireless device adjacent to or near branches of the splenic nerve of the patient. Positioning the wireless device adjacent to or near excitable tissue comprises positioning the wireless device adjacent to or near nerves within the spinal cord of the patient. Positioning the wireless device adjacent to or near excitable tissue may include positioning the wireless device adjacent to or near branches of the splanchnic nerve of the patient. Positioning the wireless device adjacent to or near excitable tissue may include positioning the wireless device adjacent to or near branches of the vagus nerve of the patient. Positioning the wireless device adjacent to or near excitable tissue may include positioning the wireless device adjacent to or near the celiac ganglion of the patient. Positioning the wireless device adjacent to or near excitable tissue may include positioning the wireless device adjacent to or near the phrenic nerve and the renal plexus of the patient. Placing the surgical instrument may include placing an endoscopic device into the torso section of the patient's body. Placing a wireless device into an opening on the surgical instrument may include placing the wireless device through a working channel or cannula of the endoscopic device. Positioning the wireless device adjacent to or near excitable tissue may include positioning the wireless device in a region in the gastro-intestinal tract or the respiratory tract of the patient. Placing the surgical instrument may include placing a catheter device into a thoracic region of the patient's body. Placing a wireless device into an opening on the surgical instrument may include placing the wireless device through a working channel or cannula of the catheter device. Positioning the wireless device adjacent to or near excitable tissue may include positioning the wireless device adjacent to or near nerves on at least one of: stomach, heart, spleen, pancreas, diaphragm, liver, or kidney of the patient.

Positioning the wireless device adjacent to or near excitable tissue may further include positioning the device adjacent to or near the pancreas of the patient, and wherein causing neural modulation to be applied to the excitable tissue comprises causing sufficient neural modulation such that inflammation is reduced in the pancreas of the patient. Causing sufficient neural modulation may further include causing sufficient neural modulation to the TRPV1 and/or CGRP-containing neurons such that inflammation is reduced in the pancreas of the patient.

Causing neural modulation to be applied to the excitable tissue may further include causing neural modulation of the sympathetic nervous system of the patient. Causing neural modulation of the sympathetic nervous system of the patient may further include causing neural activation of the greater splanchnic nerve of the patient. Causing neural modulation of the sympathetic nervous system of the patient may further include causing neural inhibition of the greater splanchnic nerve of the patient.

The method may further include using X-Ray fluoroscopy to guide positioning the wireless device adjacent to or near one or more excitable tissue. The method may further include using ultrasound sonography to guide positioning the wireless electrode lead adjacent to or near one or more excitable tissue.

Placing a wireless device may further include placing a wireless device that includes one or more non-inductive antennas configured to receive electromagnetic energy radiated from a source located outside of the patient's body, electronic circuitry coupled to each of the one or more non-inductive antennas and configured to extract electric power and excitation pulses from the radiated electromagnetic energy as received by the one or more non-inductive antennas, and one or more electrodes configured to deliver the excitation pulses to the one or more excitable tissue to effectuate the neural modulation thereof.

In another aspect, a method for stimulating nerves leaving or within the spinal cord for treating chronic visceral pain (e.g., gastroparesis, IBS, mesenteric ischemia, epigastric abdominal pain, pelvic visceral pain, familial Mediterranean fever and chronic pancreatitis, post-gastric bypass chronic pain, mesenteric ischemia, abdominal adhesions and the like), visceral pelvic pain (e.g., anterograde implantation for posterior pelvic wall, post-hysterectomy, visceral pelvic adhesions, endometriosis remission and retrograde implantation for interstitial cystitis and pelvic floor issues), pain associated with cancer, such as pancreatic cancer, and intractable angina comprises advancing one or more devices with electrodes to a target site on or adjacent to nerves leaving or within the spinal cord. One or more electrical impulses are applied to the electrodes sufficient to modulate the nerves leaving or within the spinal cord. Some implementations employ a wireless device with electrodes and an input signal containing electrical energy is delivered to an antenna coupled to the electrodes. The input signal is converted to electrical impulses and applied to the electrodes for modulating the nerves.

In some cases, the input signal is delivered by an external antenna physically separate from one or more antenna on the wireless device. The external antenna may be positioned either external to the patient's body or in a location on or in the patient's body separate from the electrodes and the one or more antennas on the wireless device. In some examples, the wireless device with electrodes is implanted at the target site. In other examples, the wireless device is percutaneously, laparoscopically or endoscopically advanced to the target site and withdrawn upon conclusion of the treatment.

In another aspect, a method for treating disorders, inflammation and/or pain comprises advancing a device into a patient's body and positioning the device adjacent to or near nerves within or leaving the spleen, stomach wall, pancreas, diaphragm or liver. In certain implementations, the device is secured to the wall of an organ to stimulate excitable tissue of the organ. In other implementations, the device is placed adjacent to or near the splenic nerve. The device may contain between one and 16 electrodes. Some implementations employ a wireless device that includes one or more antennas for receiving an input signal containing electrical energy. The input signal may be processed so that electrical pulses may be generated on the wireless device to drive power to the electrodes for modulating the nerves. The input signal may be delivered to the one or more antenna(s) on the wireless device by an external antenna positioned either external to the patient's body or in a location on or in the patient's body separate from the electrodes and the device antenna(s).

In yet another aspect, a method for treating pain and/or activating/deactivating organ functionality (e.g., kidneys, pancreas, spleen, bowel, stomach and/or liver) comprises positioning a device adjacent to or near branches of the splanchnic nerve, such as the greater, lesser or least splanchnic nerves or the celiac ganglion, particularly near the celiac artery. The positioning step may include advancing one or more devices with electrodes (e.g., through an open, endoscopic or percutaneous procedure) to a target site on or adjacent to the targeted nerves and an electrical impulse is applied to the electrodes sufficient to modulate the nerves. Some implementations may employ a wireless device and an input signal containing electrical energy may be delivered to one or more antennas coupled to the electrodes of the wireless device. The input signal may be processed by electronic circuitry on the wireless device such that electrical pulses are created on the wireless device to drive power to the electrodes for modulating the nerves. In one aspect, the input signal is delivered by an external antenna physically separate from the one or more antennas on the wireless device. The external antenna may be positioned either external to the patient's body or in a location on or in the patient's body separate from the electrodes and the first antenna. In certain configurations, the devices are implanted at the target site.

In yet another aspect, a device is positioned adjacent to or near the splenic nerve or the pancreas to treat pain and/or disorders of the spleen and pancreas. In one example, electrical pulses are applied to the device sufficient to modulate the targeted nerves and reduce inflammation (e.g., by depressing inflammatory-provoking upregulated TRPV1+Neurons) in or around the pancreas to thereby reduce pancreatic pain. Some implementations employ a wireless device.

In another aspect, a device is positioned adjacent to or near the celiac artery to modify the function of the small and/or large intestines. Some implementations employ a wireless device. In some implementations, an additional wireless device is positioned adjacent to or near the inferior mesenteric ganglia for modifying the function of the ascending and descending colon.

In another aspect, a device, such as a wireless device, is positioned adjacent to or near vagal nerve branches on the anterior-superior surface of the stomach to treat digestive conditions, type II diabetes, nausea, obesity and/or pain or inflammation. In one example, the device is secured to the external wall of the stomach. In another example, the device is secured to the lateral anterior-superior surface of the stomach.

In another aspect, a device, such as a wireless device, is positioned adjacent to or near the phrenic nerve to treat pain arising from structures innervated by the phrenic nerve, such as Kehr's sign, hiccough reflex of the diaphragm and the like. In certain implementations, the device is positioned and secured on the surface of the diaphragm to provide electrical impulses to the phrenic nerve sufficient to modulate the nerve and treat pain or inflammation.

In another aspect, a device, such as a wireless device, is positioned adjacent to or near the renal nerve plexus to treat disorders and/or pain originating from the kidneys.

In another aspect, systems and methods are described for stimulating the sympathetic nervous system (e.g., sympathetic chain ganglia, splanchnic nerves (greater, lesser, least), splenic nerves, peripheral ganglia (celiac and superior mesenteric ganglia) to treat obesity, type II diabetes and/or other eating disorders.

In another aspect, a device, such as a wireless device, is positioned on either the inner or outer heart walls to treat refractory angina. In certain implementations, the device is advanced through a cardiac catheter introduced at the femoral vein and implanted in the interior heart tissue, such as the right or left atrium wall or the right or left ventricle.

The methods described above may include providing a wireless device including an enclosure that houses one or more electrodes; a first antenna configured to receive, from a second antenna and through electrical radiative coupling, an input signal containing electrical energy, the second antenna being physically separate from the wireless device; one or more flexible circuits electrically connected to the first antenna, the flexible circuits configured to create the one or more electrical pulses suitable to be applied at the electrodes using the electrical energy contained in the input signal; and supply the one or more electrical pulses to the one or more electrodes, and wireless device into a subject's body through an introducer or a needle.

In another aspect, a system for stimulating neural tissue comprises a controller module having a first antenna external to the patient's body and configured to send an input signal containing electrical energy to a second antenna through electrical radiative coupling. The second antenna is a dipole antenna and is located in an enclosure in a wireless device, such as those described above. The wireless device may not include an internal power source. The circuits of the device may include only passive components. The input signal has a carrier frequency in the range of about 300 MHz to about 8 GHz, preferably between about 750 MHz to about 2.5 GHz.

In another aspect, a wireless device configured for stimulating nerves, such as those described above, preferably comprises an enclosure shaped and configured for percutaneous delivery into a patient's body through an introducer or needle to a target site in the patient's body. The enclosure houses one or more electrodes configured to apply one or more electrical pulses to a neural tissue. The enclosure preferably also houses a first antenna configured to receive, from a second antenna through electrical radiative coupling, an input signal containing electrical energy. In some embodiments, the second antenna is physically separate from the wireless device and may be positioned external to the patient's body. In certain exemplary embodiments, the first antenna is a dipole antenna. The enclosure further comprises one or more circuits electrically connected to the first antenna and configured to create the one or more electrical pulses suitable for stimulation of the neural tissue using the electrical energy contained in the input signal and to supply the one or more electrical pulses to the one or more electrodes.

In some embodiments, a portion of the enclosure may leave the electrodes in a non-direct contact with the neural tissue after the device has been delivered into the patient's body. The enclosure can be semi-cylindrical in shape and the device may include at least one directional electrode that directs a current path associated with the one or more electrical pulses to a direction that is substantially perpendicular to the neural tissue. The devices may include a semi-cylindrical array of electrodes. The electrodes may be made of at least one of platinum, platinum-iridium, gallium-nitride, titanium-nitride, iridium-oxide, or combinations thereof. The devices may include two to sixteen electrodes, each having a longitudinal length between about 0.25 and 6.0 mm and a diameter between about 0.1 and 0.8 mm. The electrodes are spaced between about 0.25 mm to 6 mm apart and have a combined surface area of between about 0.19 $mm^2$ to 250.0 $mm^2$.

BRIEF DESCRIPTION OF THE DRAWINGS

FIG. 16A illustrates an example suction stylet in zero pressure mode.

FIG. 16B illustrates the example suction stylet in first level of negative pressure mode.

DETAILED DESCRIPTION

In various implementations, a neural stimulation system and method is disclosed for applying one or more electrical impulses to targeted nerves for treating chronic pain, inflammation and/or disorders, such as visceral pain (e.g., gastroparesis, IBS, mesenteric ischemia, epigastaric abdominal pain, pelvic visceral pain, familial Mediterranean fever and chronic pancreatitis, post-gastric bypass chronic pain, mesenteric ischemia, abdominal adhesions and the like), visceral pelvic pain (e.g., anterograde implantation for posterior pelvic wall, post-hysterectomy, visceral pelvic adhesions, endometriosis remission and retrograde implantation for interstitial cystitis and pelvic floor issues), inflammation and pain associated with cancer, such as pancreatic cancer, intractable and/or refractory angina, organ functionality, type II diabetes, eating disorders, motility, gastroparesis, reflux, obesity, nausea, and the like. The targeted nerves can include, but are not limited to, the spinal cord, nerves on the inner and outer walls of the stomach and heart, the sympathetic nervous system (e.g., sympathetic chain ganglia, splanchnic nerves (greater, lesser, least), splenic nerves, vagal nerves, the renal plexus, glossopharyngeal nerves, peripheral ganglia (celiac and superior mesenteric ganglia), nerves on the external diaphragm, stomach, heart, liver, kidneys, pancreas, spleen and the like.

Various embodiments can also include distinct advantages over wired leads with regard to ease of insertion, cross connections, elimination of extension wires, and no requirement for an implantable pulse generator in order to administer a chronic therapy. Various implementations also may have an associated lower overall cost compared to existing implantable neural modulation systems due to the elimination of the implantable pulse generator and this may lead to wider adoption of neural modulation therapy for patients as well as reduction in overall cost to the healthcare system.

Figure 1A:
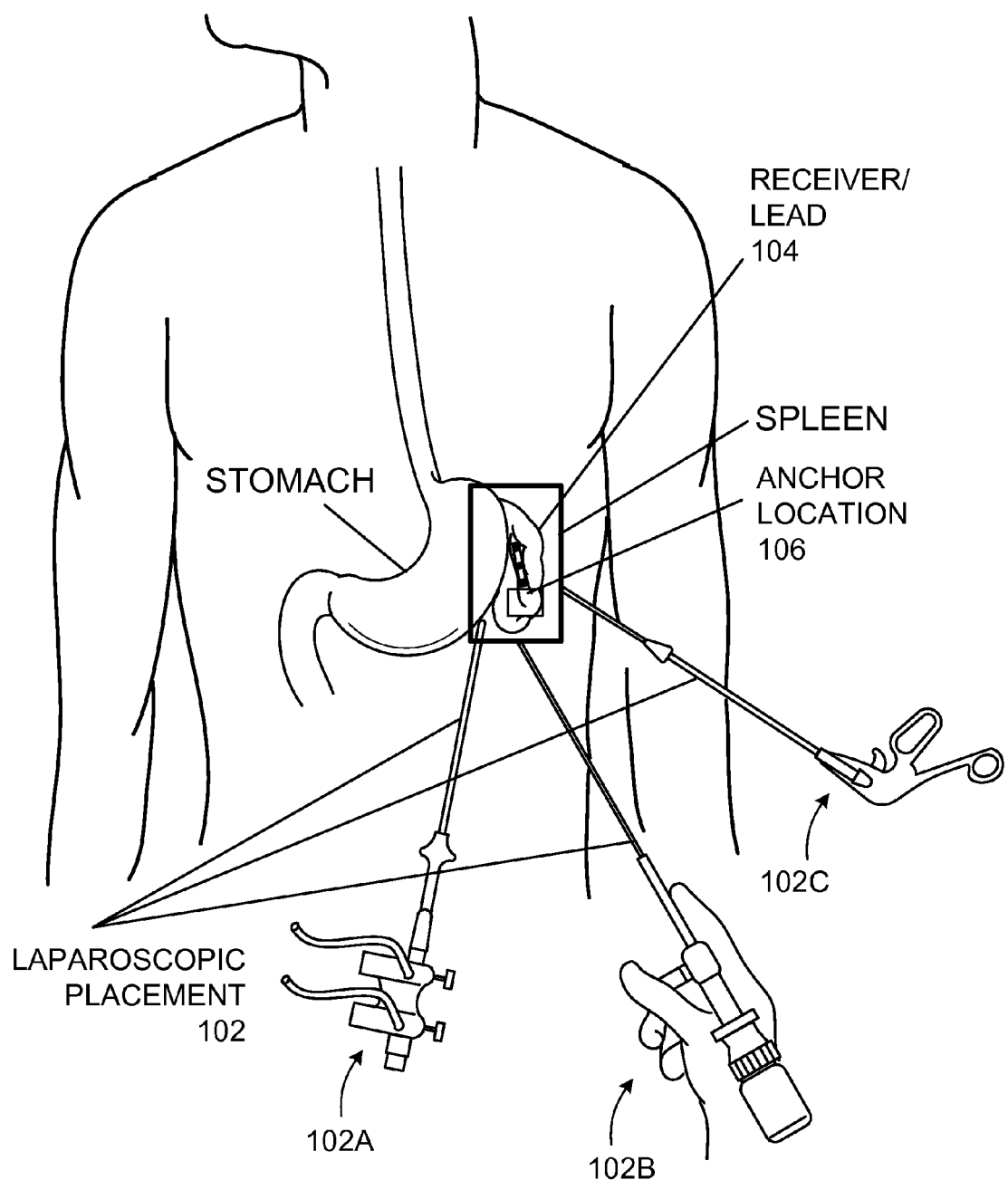
FIG. 1A illustrates a device placement at the spleen via laparoscopic operation.

Referring now to FIG. 1, a system and method for implanting a wireless device adjacent to or near the spleen is illustrated. As shown, the wireless device 102 is advanced into the abdominal cavity by laparoscopic placement 102 and through a laparoscopic incision on the patient's body. In some instances, a laparoscopic device, such as devices 102A, 102B, or 102C, may be placed at the incision site. For stimulation of the splenic nerves, the wireless device 104 may be traversed through a working channel or cannula of the laparoscopic device. Once inside the abdominal cavity of the patient's body, the device may be placed, for example, perpendicular to the lateral traversing splenic nerve. In another example, wireless device 104 may be placed in any 360° orientation relative to the splenic nerve. The device may be sutured to the serous coat of the spleen. In still other implementations, the device may be sutured or secured to alternate organs like the exterior stomach wall, pancreas, diaphragm, or liver. Rather than laproscopic placement, the wireless device can be positioned through a variety of other approaches, including endoscopic or open surgical techniques. The placement procedure may be conducted under imaging guidance, such as X-Ray fluoroscopy or ultrasound sonography. Once wireless device 104 has been placed at the target location in the abdominal cavity, The wireless device 104 is anchored to nearby tissue, for example, anchor location 106, to stimulate excitable tissue near the spleen.

The device may contain, for example, at least two electrodes and be about 3 cm long with a feature for suturing the lead to surrounding tissue. The device may be used for visceral treatments and may contain between one and sixteen electrodes. The device and the electrodes thereon may have an outer diameter from between 0.1 mm to 1.35 mm. The length of the electrodes may be from between 0.5 mm to 6.0 mm. The total electrode lead length may be from between 10 mm and 600 mm. Internal to the device is one or more electronic circuits that receive power for stimulation from a wireless transmitter, as described above and below. The device may include, an anchoring feature to allow for suturing to tissues using a biocompatible nylon thread. The suture feature of the device may include a hole through the insulation material with a diameter from between 0.1 mm and 1 mm. The device body insulation may include concave suture channels with a diameter from between 0.1 and 0.5 mm diameter smaller than the device body's outer diameter.

Figure 1B:
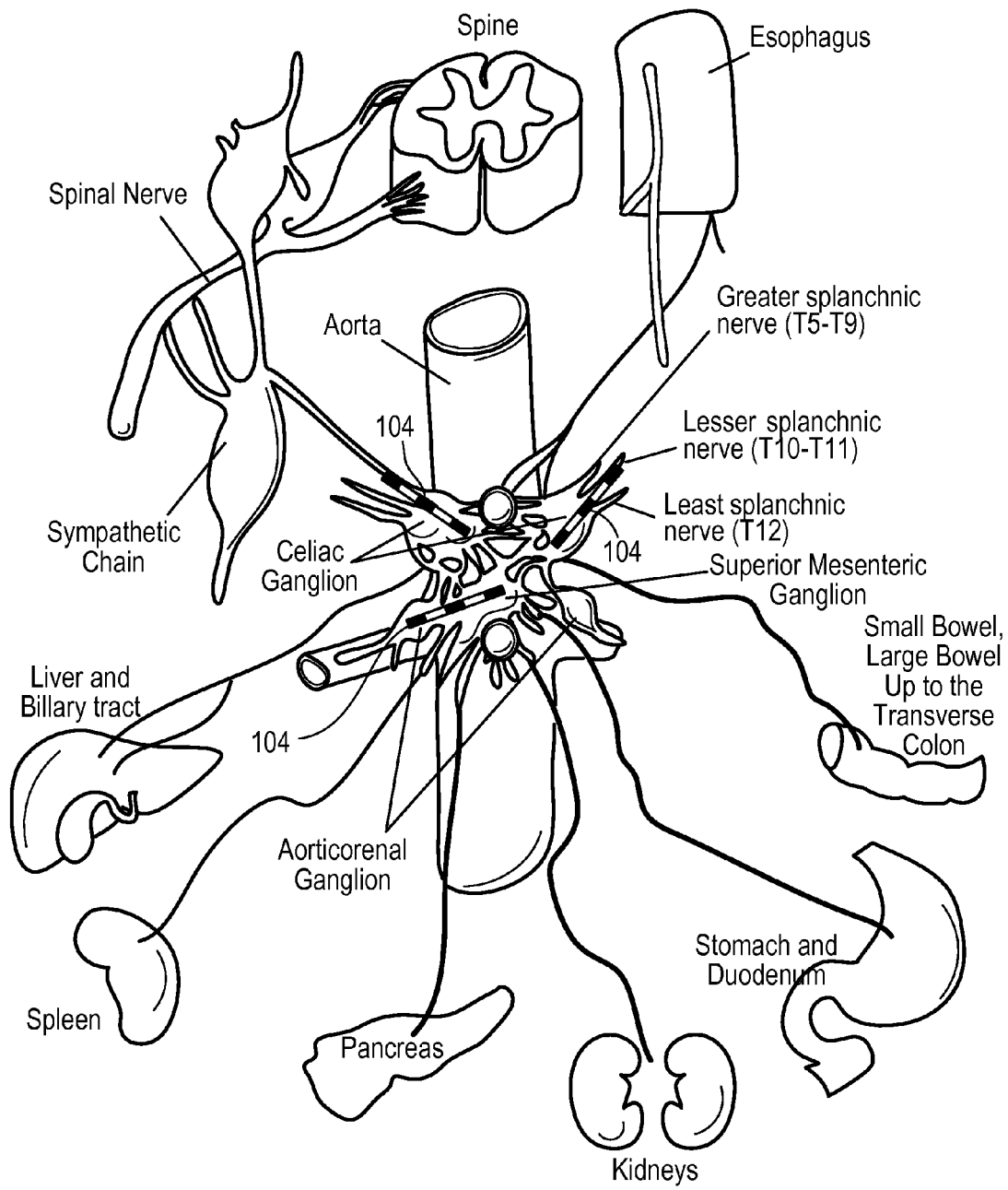
FIG. 1B. illustrates a device placement at the splanchnic nerve bundle with affected organs.

FIG. 1B illustrates the organs affected by stimulation of the splanchnic nerve bundle. As illustrated, the wireless device 104 can be implanted adjacent to or near the splanchnic nerve bundle to modulate one or more of the splanchnic nerves (including, for example, lesser, greater or least splanchnic nerves). The placement procedure may include a laparoscopic procedure, such as the procedure described above.

Nerves travelling from the spine to the celiac ganglion include the great splanchnic and the small splanchnic nerves (for example, at spinal levels T5-T12). The splanchnic branches from the spinal cord congregate to meet at the celiac ganglion before the nerves connect to the organs. Stimulation at the celiac ganglion may include one or more wireless devices that can be placed around the celiac artery, as illustrated in FIG. 1B. The celiac artery has been shown to have a diameter from between 6.0 mm to 8.0 mm.

Stimulation at the celiac ganglion can affect, for example, the esophagus, the bowel, the stomach, the kidneys, pancreas, spleen, or liver neural pathways. This stimulation site may be applicable in a variety of indications such as pain, activating/deactivating organ functionality or obesity.

The sympathetic nervous system plays an important role in obesity. For example, drugs that activate the sympathetic nervous system are known to increase energy expenditure, which can result in weight loss. Similarly, electrical activation of the sympathetic nervous system can help to treat obesity. Electrical modulation (inhibition or activation) of the sympathetic nervous system can also be used to treat other eating disorders, such as anorexia or bulimia.

To treat obesity, some implementations may include electrical stimulation or activation of the greater splanchnic nerve. Typically, lower frequency (on the order of 1 to 50 Hz) stimulation may result in activation of the sympathetic nervous system and high frequency (greater than 100 Hz) stimulation may result in inhibition.

Electrical modulation of the sympathetic nerves may also be used to treat gastrointestinal diseases or disorders, such as type II diabetes, peptic ulcers, esophageal reflux, gastroparesis and Irritable Bowel Syndrome (IBS). Stimulation of the splanchnic nerves that innervate the large intestine may reduce symptoms of IBS, characterized by diarrhea.

The greater splanchnic nerve (GSN) is formed by efferent sympathetic neurons exiting the spinal cord at T4 or T5. Postganglionic neurons from the celiac ganglia that synapse with the GSN innervate primarily the upper digestive system, including the stomach, pylorus, duodenum, pancreas and liver. Postganglionic nerves of the mesenteric ganglia (supplied by nerves from the lesser and least splanchnic nerve), innervate primarily the lower intestine, colon, rectum, kidneys, bladder and sexual organs.

Figure 1C:
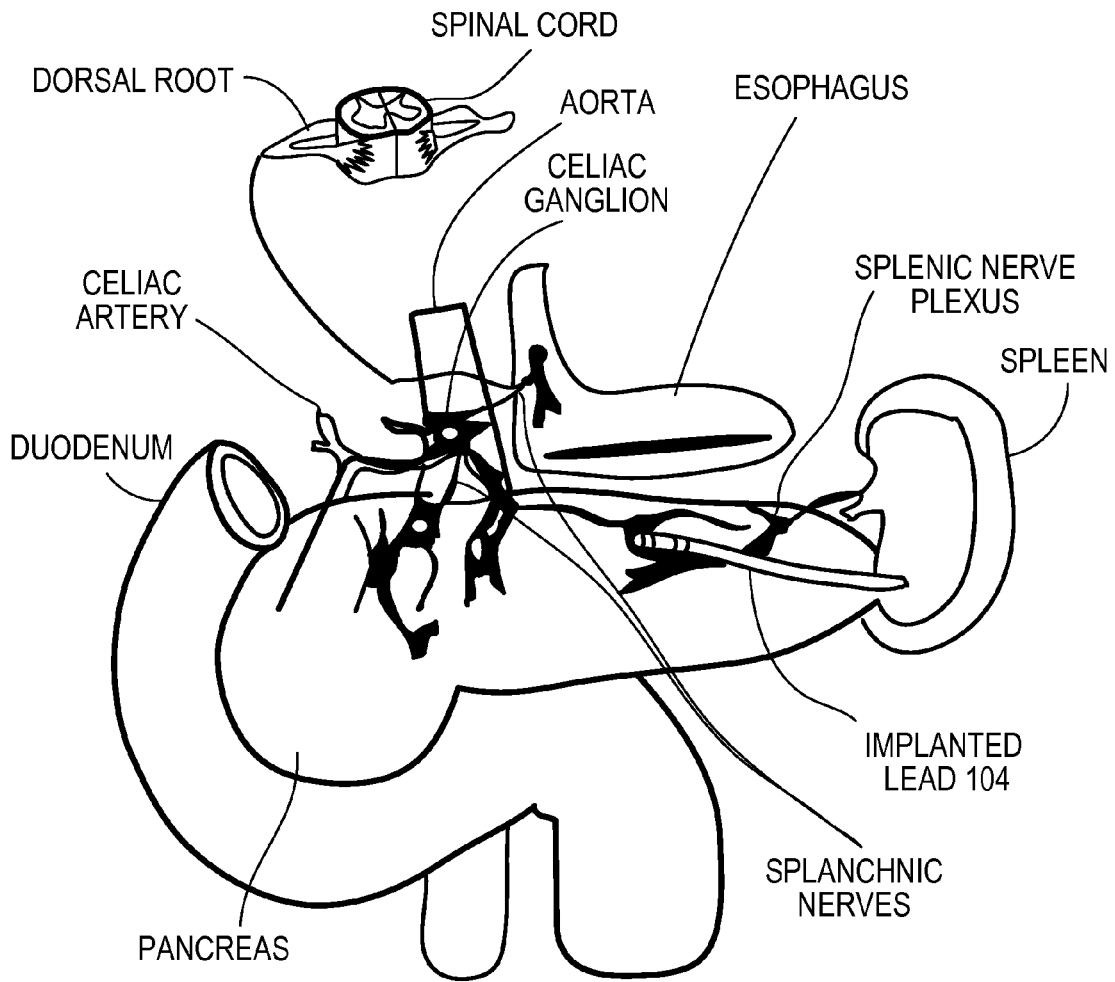
FIG. 1C illustrates a device placement at the splanchnic nerve for spleen stimulation.

FIG. 1C illustrates a wireless device 104 implanted near or adjacent to the splenic nerve plexus for modulating such plexus to treat the spleen. In some implementations, a wireless device (such as a miniature device as described below with respect to FIGS. 10-23D) is implanted parallel with the splenic nerve plexus on top surface of the pancreas. The wireless device may be implanted through a laparoscopic procedure where the device is introduced to the body through a cannula or working channel, similar to the procedure described above in association with FIG. 1A. As part of the operation, the laparoscopic instruments retract the liver and stomach laterally to gain direct access to the pancreas. Treatment of the splenic nerve plexus can affect the spleen and the pancreatic neural pathways. The wireless device may include a proximal tail of empty tubing that can be sutured to surrounding tissue or tunneled to a subcutaneous level for anchoring. Placement of the wireless device on the top surface of the pancreas may stimulate the splenic nerve bundles, which may broadly affect connected organs such as the pancreas, the spleen, and the vagus nerve.

Figure 2:
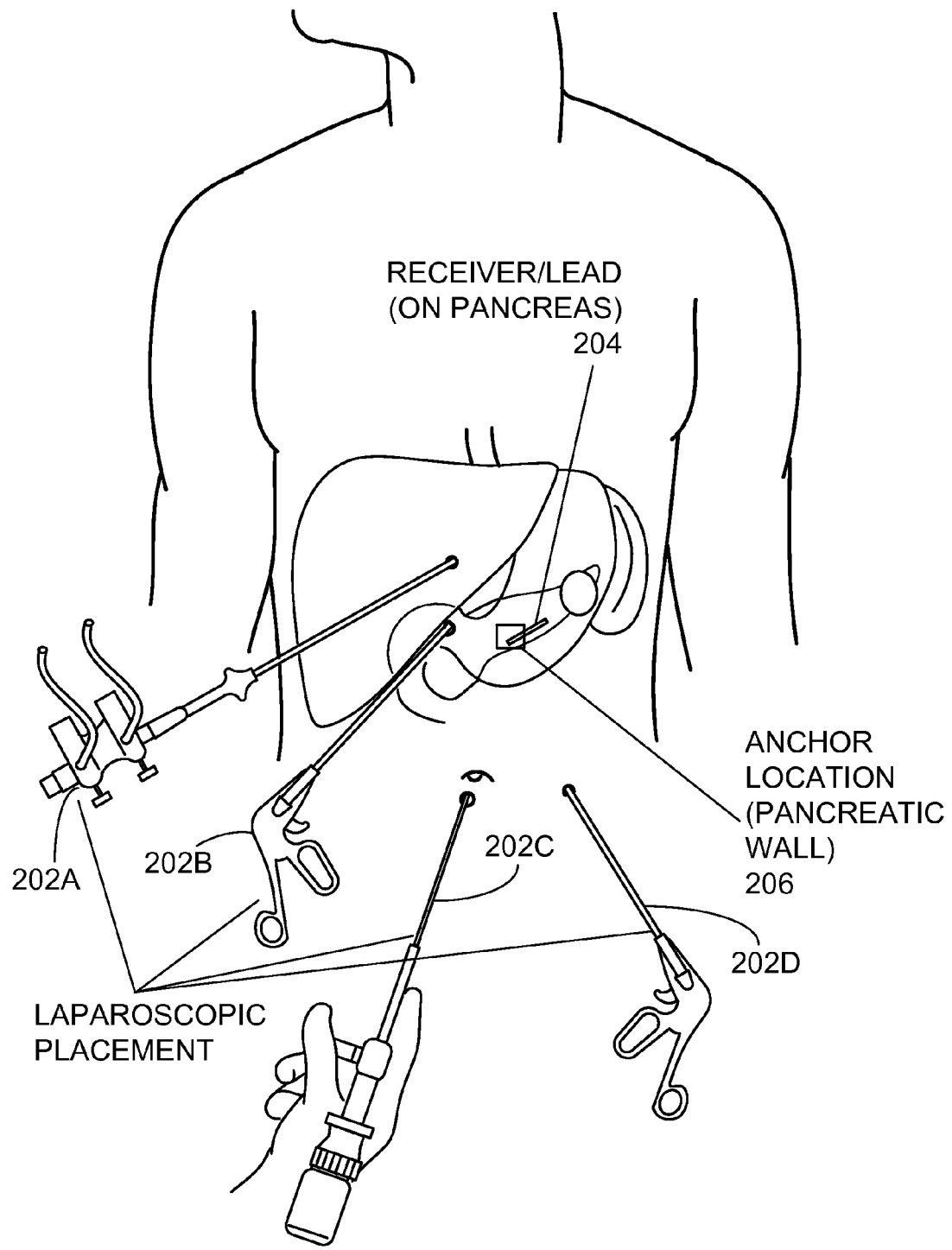
FIG. 2 illustrates a device placement at the pancreas via laparoscopic operation.

Referring now to FIG. 2, another location for placing a wireless device may include the ventral surface of the pancreas. When the wireless device is placed on the ventral surface of the pancreas, the wireless device is in the space between the pancreas and the stomach. Placing the wireless device on the ventral aspect of the pancreas may deliver a targeted treatment focusing on stimulating solely the pancreas and stomach's neural pathways. A physician may insert a laparoscopic device, such as device 202A, device 202B, device 202C, or device 202D, into a patient's abdominal cavity through an incision site. Thereafter, the physician may advance wireless device 204 through a working channel or cannula of the laparoscopic device to reach a target area, for example, a location on the ventral surface of the pancreas. Once wireless device 204 has reached the target location, for example, a location on the ventral aspect of the pancreas, the physician may anchor the wireless device 204 at anchor location 206 (for example, on the pancreatic wall).

Pancreatic pain is a relatively common and disabling clinical condition usually caused by inflammation. Inflammation increases tissue temperature and promotes acidification of tissue; both stimuli excite TRPV1- and CGRP-containing neurons. This adverse milieu creates an environment due to up regulation of TRPV1 neurons leading to hyperalgesia and excessive blood flow. Both acute and chronic inflammation can cause these nerves to become sensitized so that more and more local cells (including dorsal horn neurons) express the TRPV1 receptor. Antagonists against TRPV1 and CGRP may be useful in attenuating the pain state. It is anticipated that physiological methods aimed at desensitizing TRPV1 neurons at or about the relevant thoracic dorsal horns, i.e., by epidural spinal cord stimulation, will effectively curtail the pain state. This therapy will be more functionally useful and certainly should cause fewer side effects than pharmacotherapies.

Figure 3A:
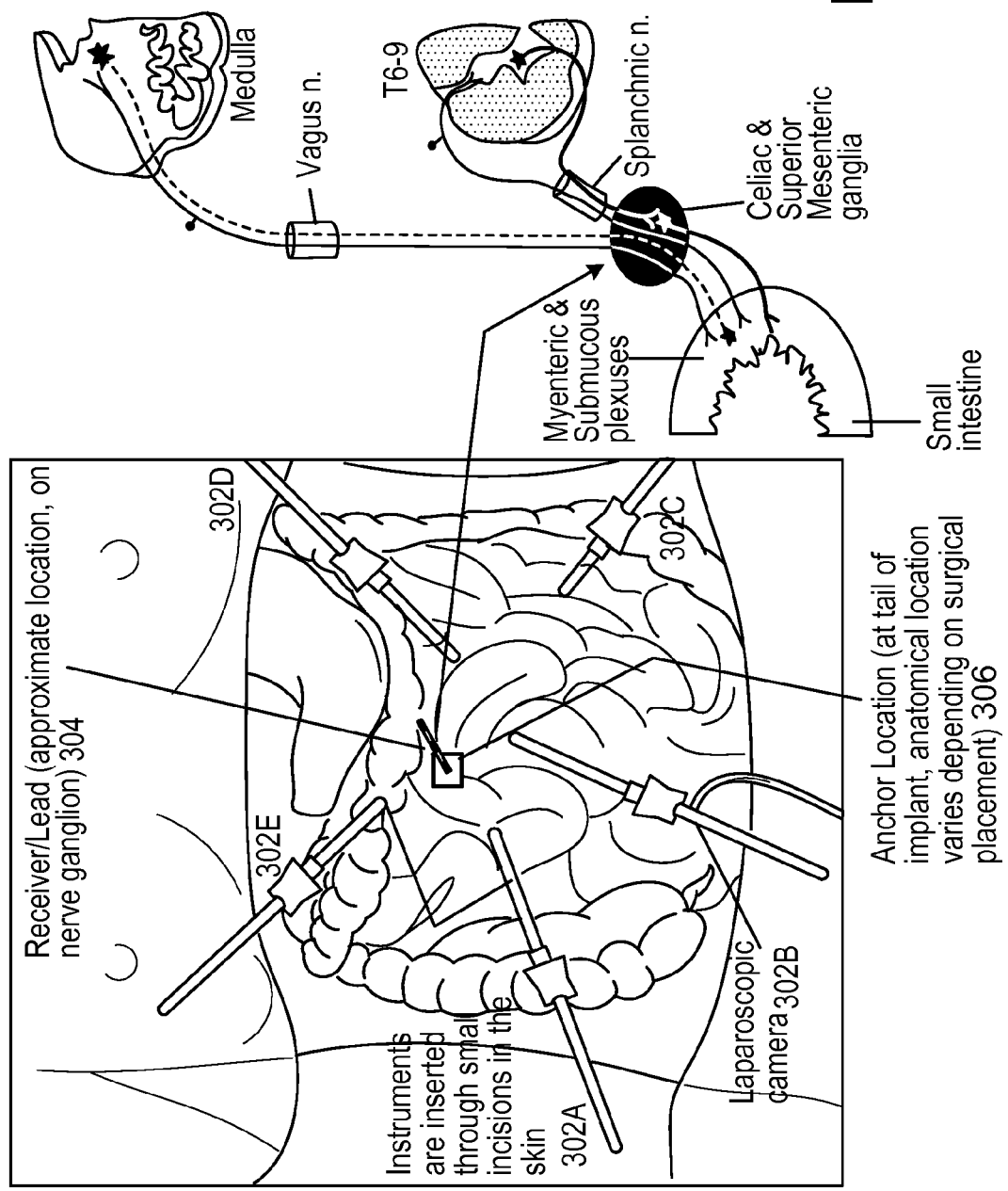
FIG. 3A illustrates a device placement in the abdomen for small intestine stimulation via laparoscopic operation.

FIG. 3A illustrates a device placement in the abdomen adjacent to or near the celiac and superior mesenteric ganglia for treating the small intestine stimulation via laparoscopic operation. In this example, wireless device 304 is placed near the celiac ganglia through a laparoscopic procedure to target the function of the small intestine. A physician may insert a laparoscopic device, such as device 302A, device 302B, device 302C, or device 302D, into a patient's abdominal cavity through an incision site. Thereafter, the physician may advance wireless device 304 through a working channel or cannula of the laparoscopic device to reach a target area, for example, the celiac ganglia. Once wireless device 304 has reached the target location, the physician may anchor wireless device 304 by, for example, suturing wireless device 304 to the tissue surrounding celiac artery. In some instances, wireless device 304 includes a tail. The physician may route the tail to a subcutaneous level and suture the tail to a subcutaneous tissue. Placing the wireless device near the celiac ganglia can affect the neural pathways and tissue function of the small and large intestine.

Figure 3B:
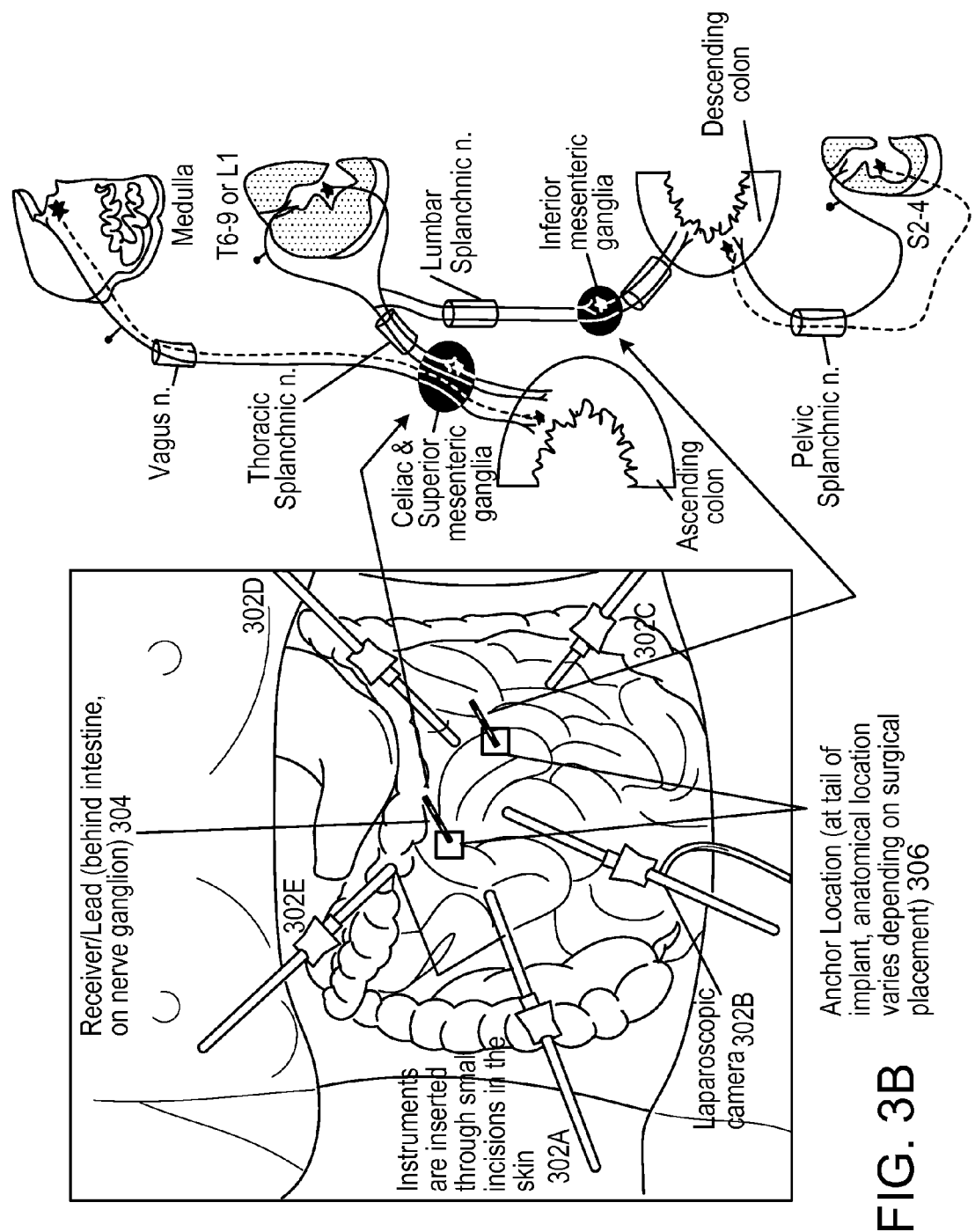
FIG. 3B illustrates a device placement in the abdomen for large intestine stimulation via laparoscopic operation.

Referring now to FIG. 3B, a wireless device 304 may be placed in the same celiac ganglion location with an additional wireless device 304 secured at the inferior mesenteric ganglia. The additional wireless device 304 may be placed by the physician during the same laparoscopic procedure or during a follow-up laparoscopic procedure, for example, when the patient has manifested a need for additional stimulation. The combination of the two wireless device 304 in FIG. 3B may produce a more targeted stimulation for the ascending and descending colon.

Figure 4A:
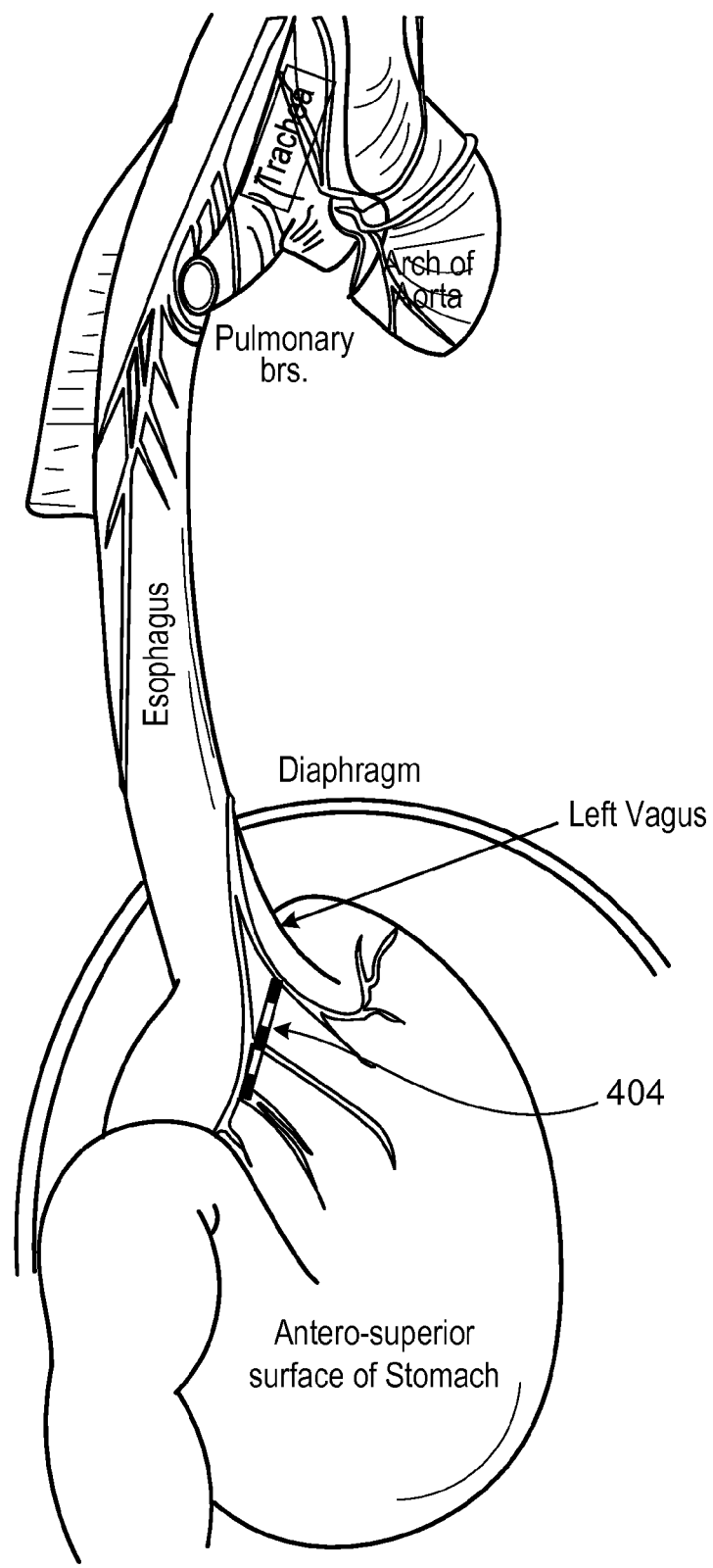
FIG. 4A illustrates a device placement at the gastro distribution of the glossopharyngeals.

In FIG. 4A, a wireless device 402 is placed onto the vagal nerve branches on the anterior-superior surface of the stomach. Using laparoscopic procedures such as the ones described above, a physician may place wireless device 404 on a target location on the anterior-superior surface of the stomach. The physician may secure wireless device 402 in place by, for example, suturing the lead to the stomach's exterior surface. The wireless electrode lead 402 may include a tail. In some instances, the physician can route the tail to a surrounding organ before suturing the tail to the surrounding organ (e.g., the abdominal wall). In some instances, the treating physician may route the tail to the subcutaneous level and before suturing the tail at the subcutaneous level. Subcutaneous suture may enable easier removal of the implanted device.

Figure 4B:
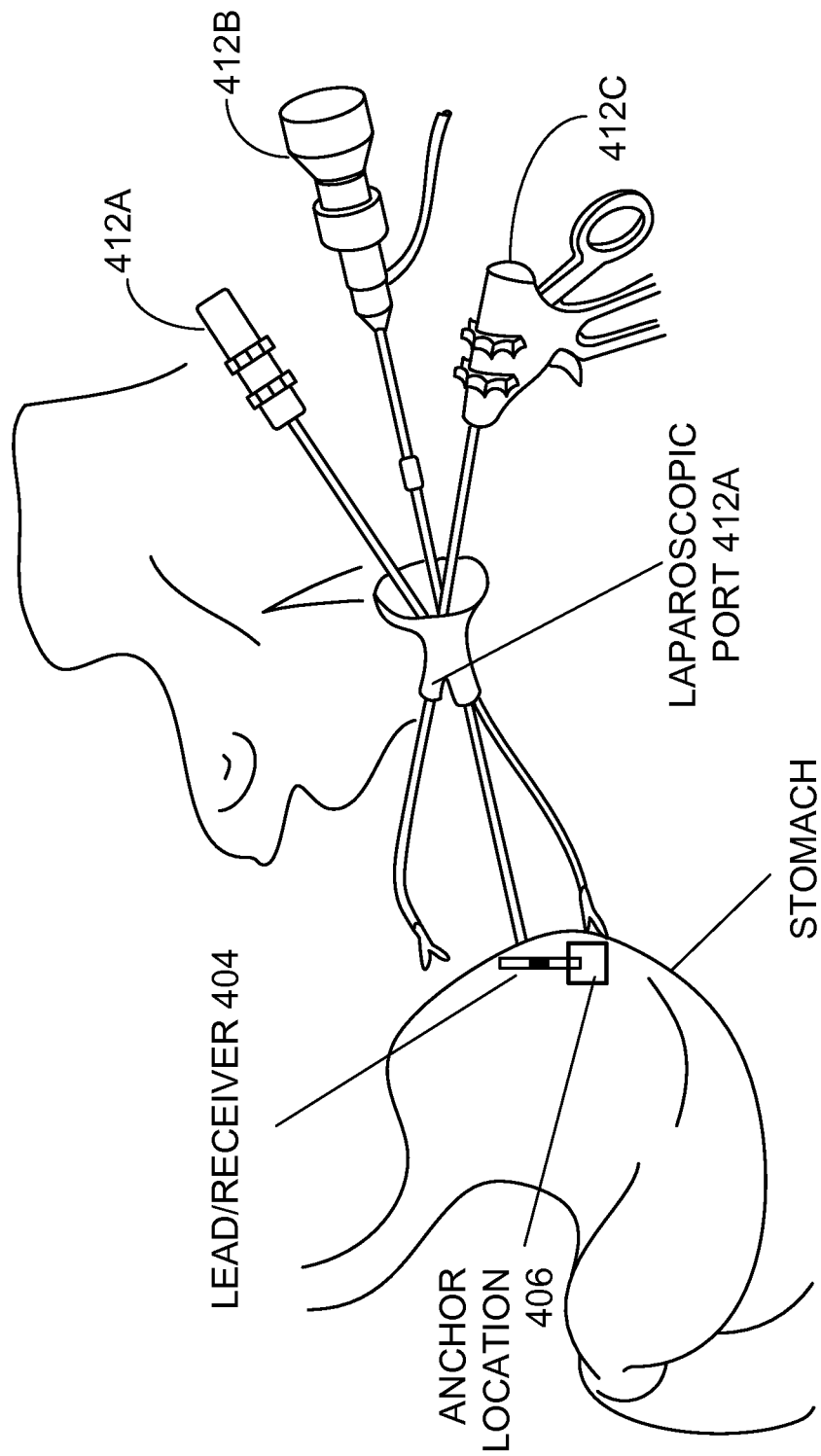
FIG. 4B illustrates a device placement at the internal gastro wall via endoscopic operation.

In another implementation illustrated in FIG. 4B, the wireless device 404 may be placed on the lateral anterior-superior surface of the stomach. In this example, wireless device 404 is placed at the external wall of the stomach through a laparoscopic delivery approach, similar to the ones described above. With the wireless device placed laterally, the gastrointestinal mechanisms of the stomach can be affected. This placement may be common for treatment of obesity. The wireless device may be sutured directly to the exterior stomach wall. The wireless device 404 may also include tines that probe into the tissue wall when the wireless device 404 is pulled in the opposing direction of insertion.

Figure 4C:
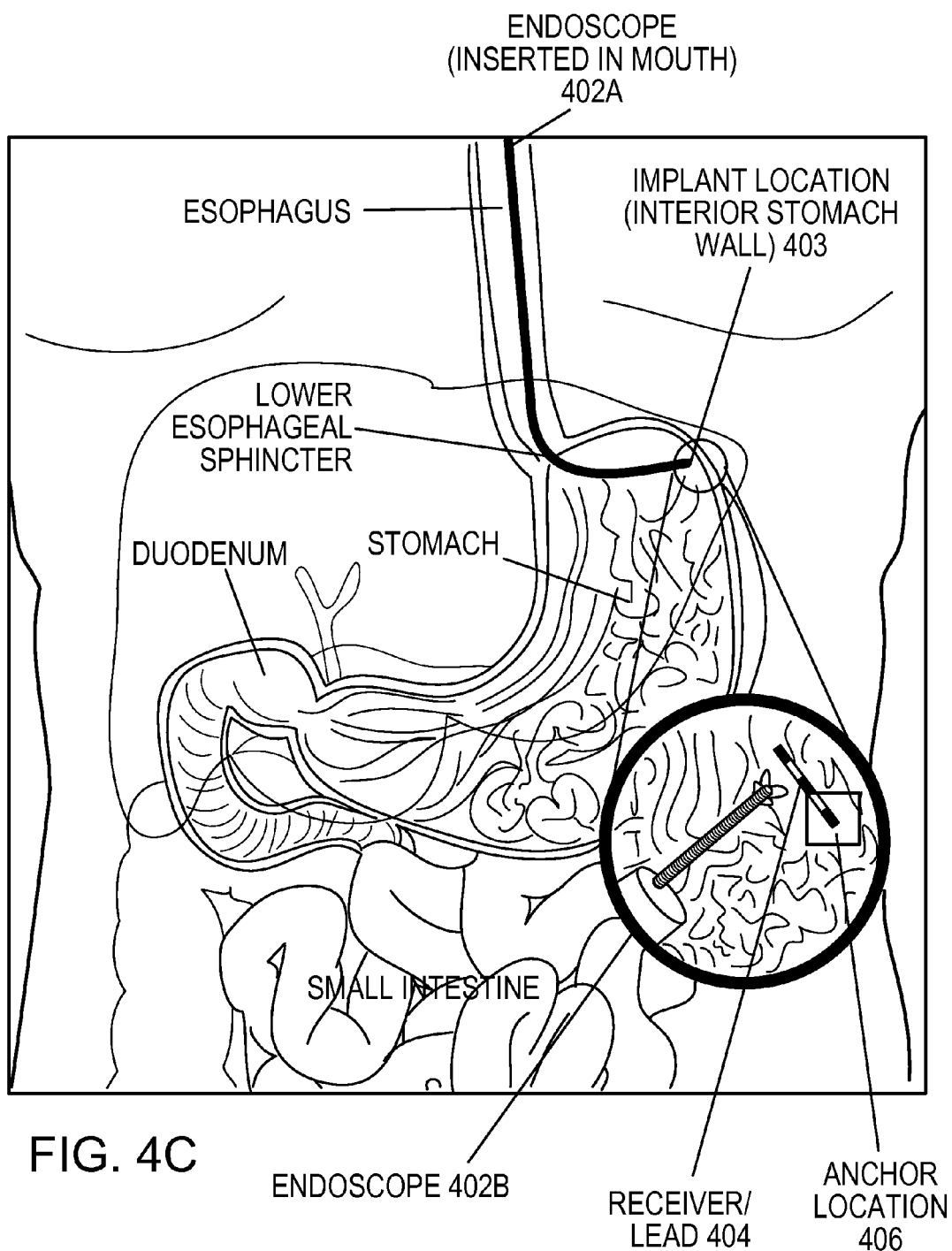
FIG. 4C illustrates a device placement at the external gastro wall via laparoscopic operation.

FIG. 4C illustrates a wireless device 404 placed at the internal gastro wall through an endoscopic operation through the esophagus for treating digestive disorders or conditions, nausea, obesity, motility or pain symptoms. A physician may insert an endoscope with a working channel through the oral cavity (mouth) of the patient and push the endoscope to reach the stomach cavity of the patient. The physician may then advance wireless device 404 down the working channel of the endoscope to place the wireless device 404 in the target location inside the stomach. The physician may then suture the wireless device 404 to the interior stomach wall using a suturing tool. The wireless device 404, however, may be deployed using a variety of approaches (open, endoscopic, or laparoscopic).

Figure 5:
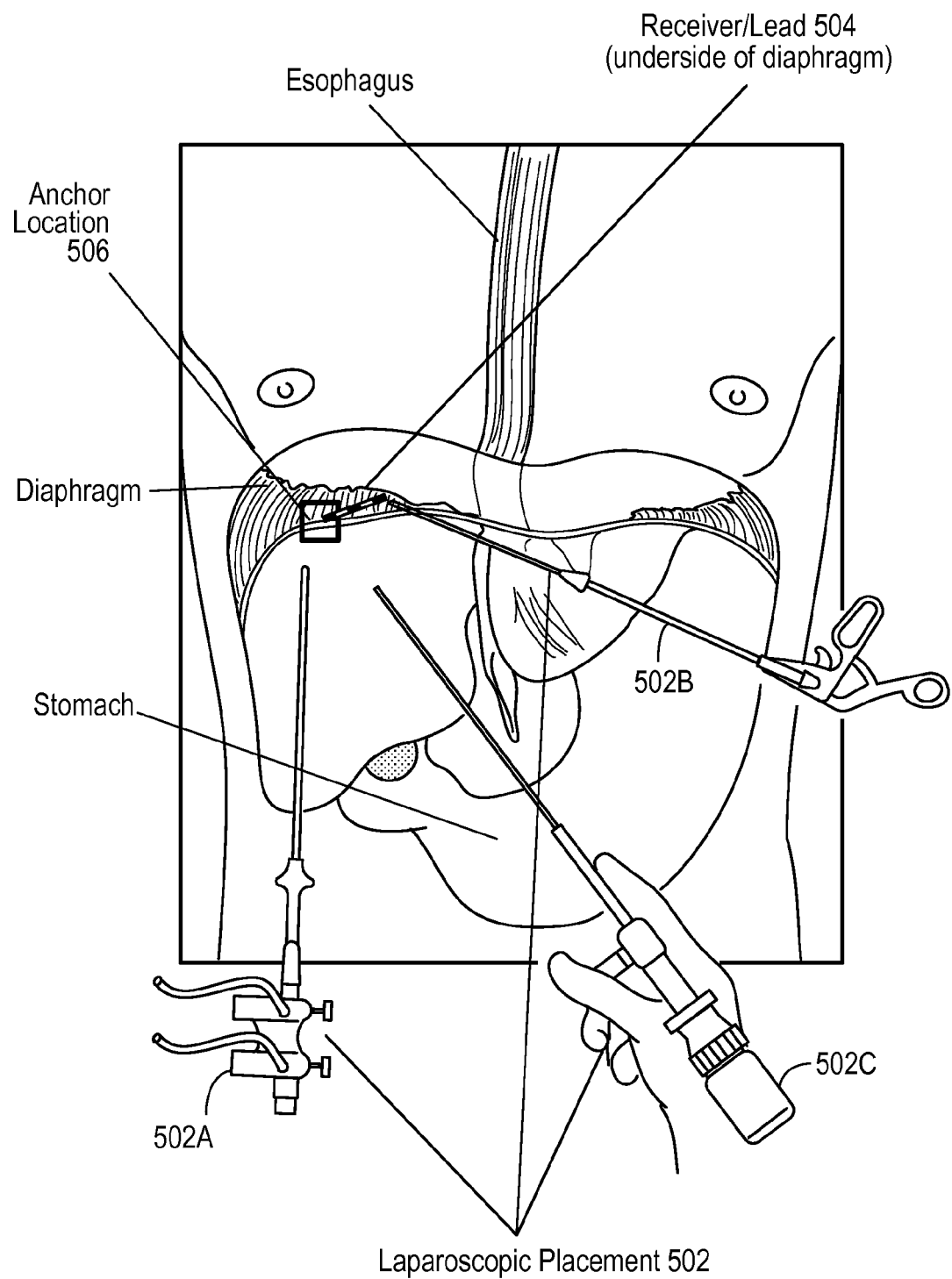
FIG. 5 illustrates a device placement at the external diaphragm wall via laparoscopic operation.

FIG. 5 illustrates a wireless device 504 placed at the external diaphragm wall through laparoscopic surgery. The wireless device 504 may be placed ventral to the liver on the caudal concave surface of the diaphragm. In one example, the physician may use laparoscopic devices, for example, devices 502A, 502B, or 502C, to retract the liver caudally to gain workable space underneath the diaphragm. The physician may then advance wireless device 504 through a working channel or cannula of a laparoscopic device, for example, devices 502A, 502B, or 502C, to place wireless device 504 along the coronal plane of the diaphragm to target the phrenic nerve. The physician may suture wireless device 504 directly to anchor location 506, for example, the diaphragm or the nearby exterior wall of the liver using standard laparoscopic instruments.

Figure 6A:
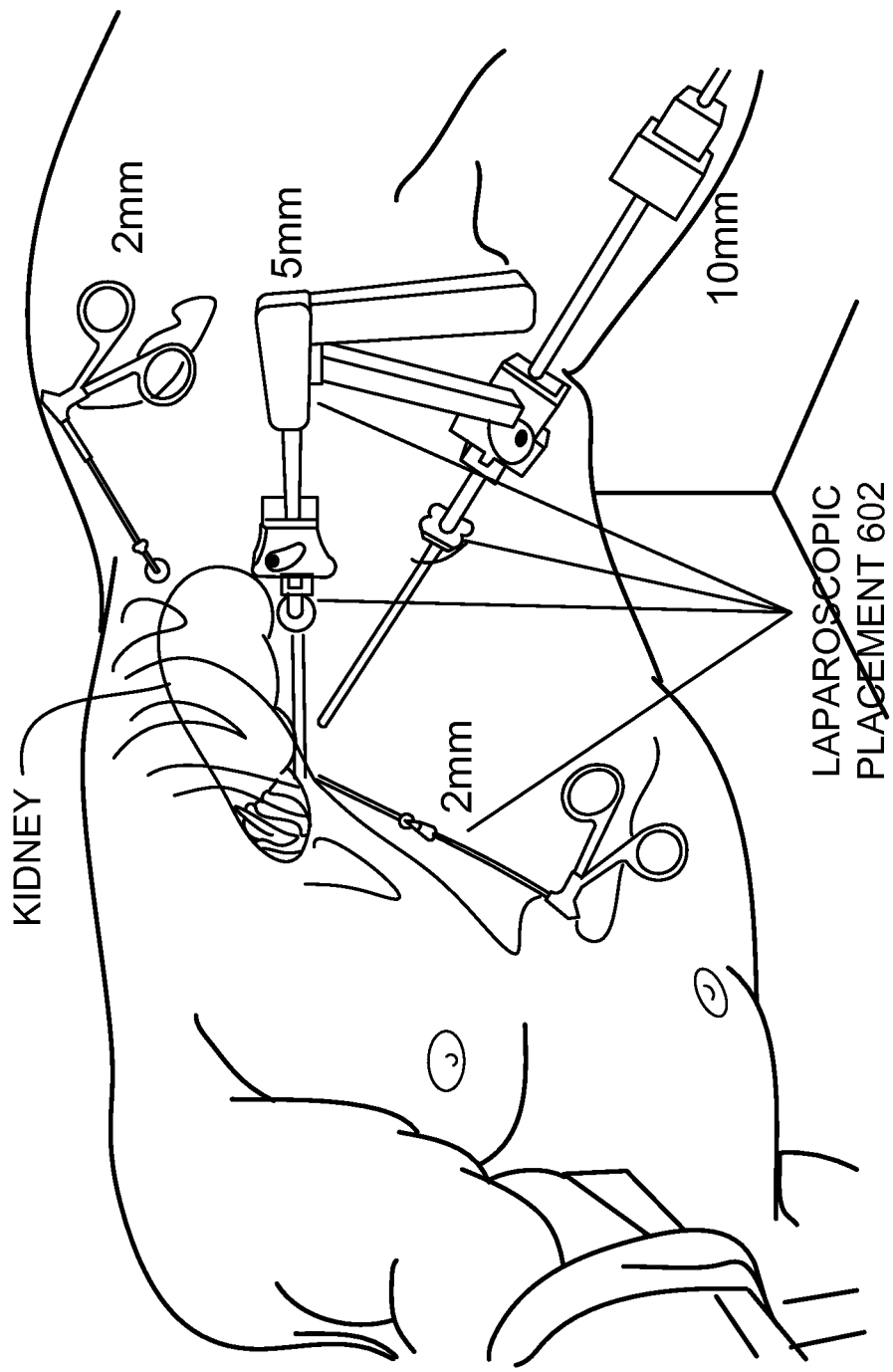
FIG. 6 illustrates a renal device placement via laparoscopic operation.
Figure 6B:
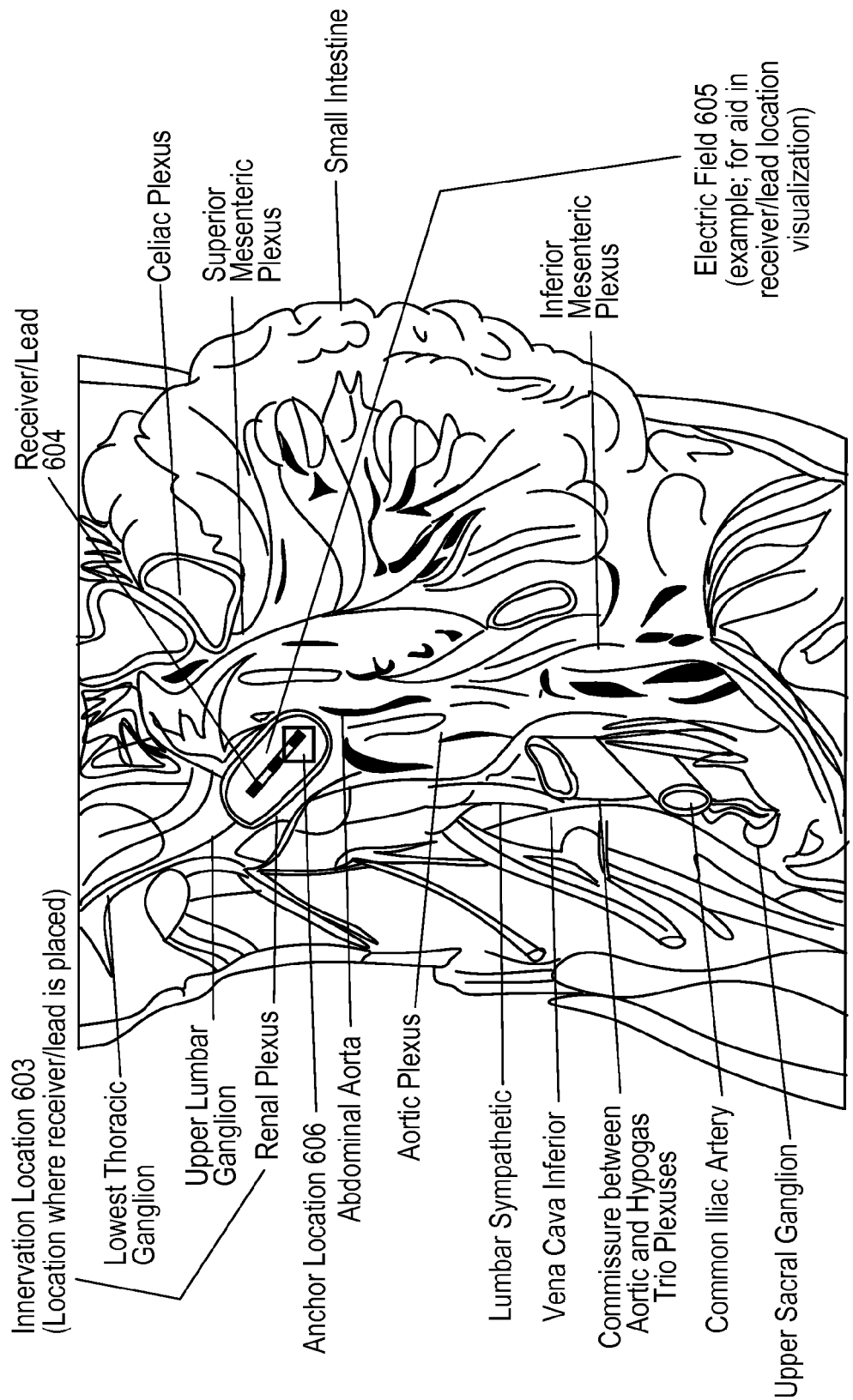

FIG. 6A-6B illustrate a wireless device 604 placed near the kidney to target the renal plexus stimulation through laparoscopic surgery. For the operation, the patient may be laid on his or her side for the physician to gain lateral access to the kidney. As illustrated in FIG. 6A, the laparoscopic surgery may use a variety of laparoscopic devices of different sizes. In one example, the physician may use the laparoscope to infiltrate the patient's body at the navel location. Thereafter, the physician may route the laparoscopic devices around and underneath the ribcage to reach the renal organs. The physician may then advance wireless device (604 along a working channel or cannula of a laparoscopic device to place wireless device 604 parallel with the renal artery to target the renal plexus, which travels along the artery. The physician then may secure wireless device 604 by suturing wireless device 604 to surrounding tissues in accordance with the descriptions herein.

Figure 7A:
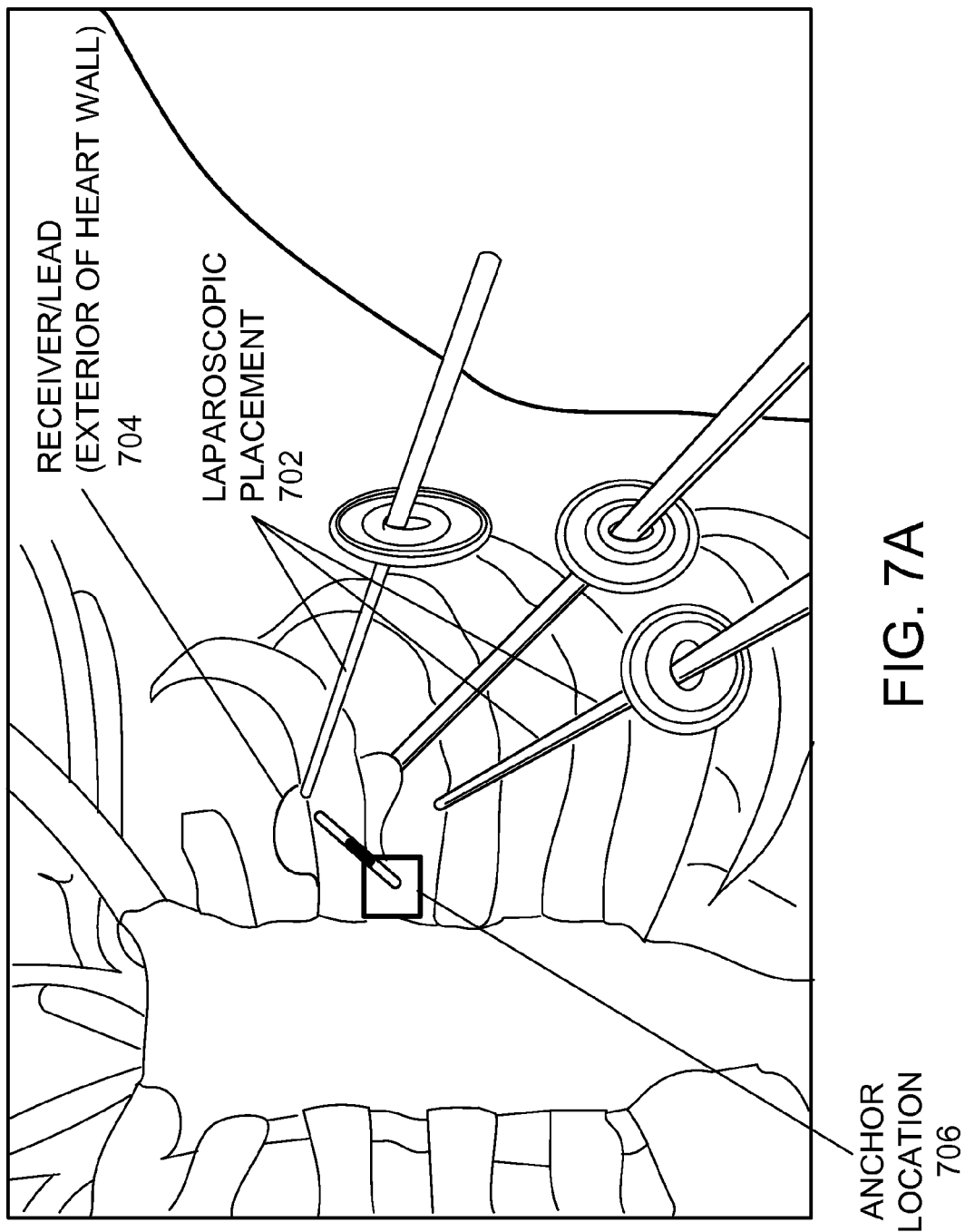
FIG. 7A illustrates an external cardiac device placement via laparoscopic operation.

FIG. 7A illustrates an external cardiac wireless device 704 placed near the vagus nerve through laparoscopic surgery. For the placement operation, the patient is laid on his or her side for a physician to gain direct access to his or her side. The physician may use laparoscopic device to infiltrate the patient's side. The physician may then pass laparoscopic instruments 702 through the ribcage of the patient to reach the exterior of the heart. The physician may then advance wireless electrode lead 704 along a working channel or cannula of a laparoscopic device to reach the exterior wall of the heart and place wireless device 704 parallel with the vagus nerve. The physician may then suture the wireless device 704 by suturing the device to surrounding tissue. In some instances, the wireless device 704 may include a tail and the physician may route the tail subcutaneously for suturing. The wireless device body may also contain cuff arms, which can secure the wireless device to the nerve, circumferentially, without puncture as seen in FIG. 8A-8B.

Figure 7B:
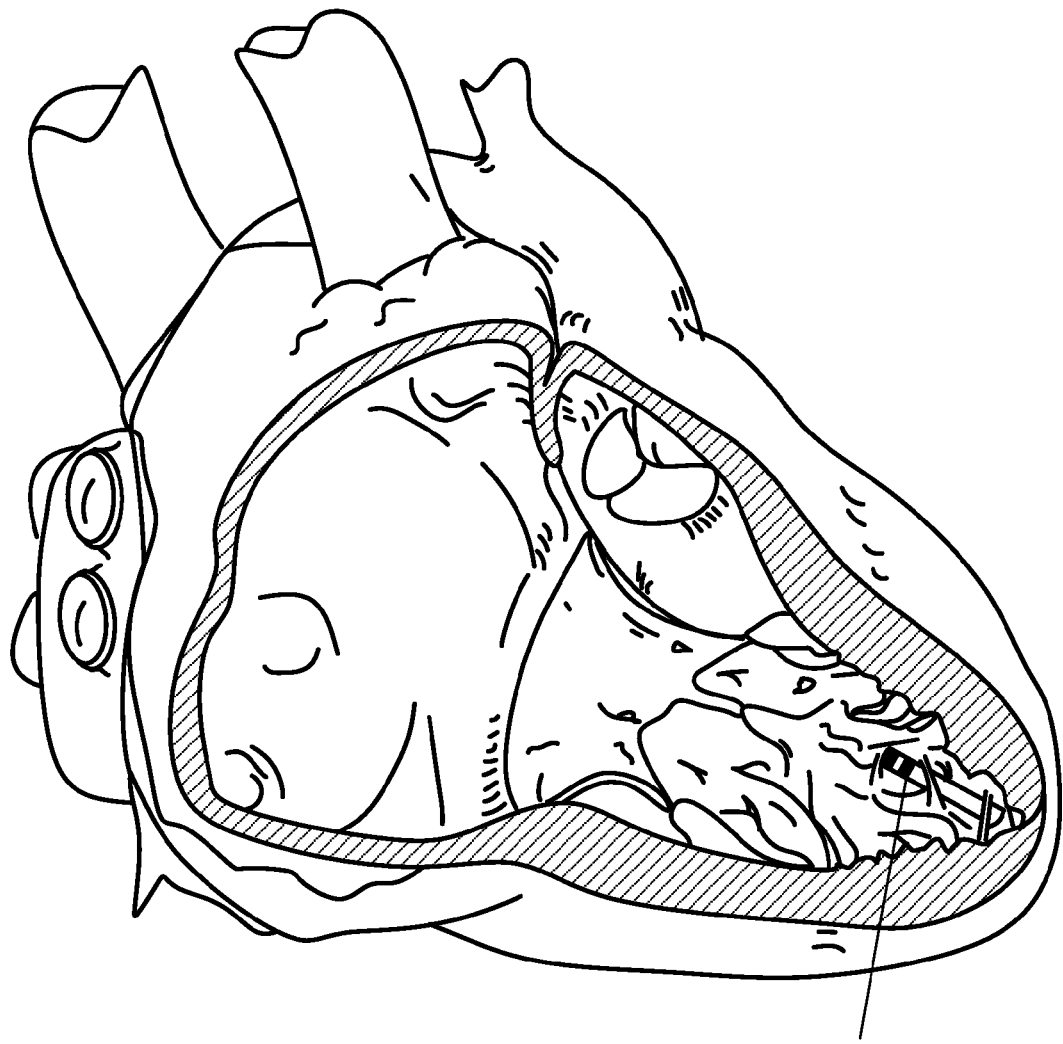
FIG. 7B illustrates an internal cardiac device placement via femoral catheter operation.

As illustrated in FIG. 7B, a wireless device 704 is secured into the cardiac muscle wall on the inside of a heart. The wireless device 704 can be placed through a cardiac catheter introduced at the femoral vein, a similar process to introducing pacing leads. The cardiac catheter may have a length from between 90 cm and 120 cm. The cardiac catheter may have an inner diameter from between 1.0 mm and 3.0 mm. The physician may advance wireless device 704 up the length of the catheter to reach a target site, for example, the inner wall of the left ventricle. The physician may then secure wireless device 704 into the muscular wall of the heart. The wireless device can be placed at various locations in the interior heart tissue, for example, the right atrium wall, right ventricle, left atrium, and left ventricle. For in-chamber placement, the wireless device may be advantageous because no obtruding connecting tube is routed through two or more chambers (for example, to an implantable battery). In other implementations, the wireless device 704 may have a tail attached which is left outside of the heart for retrieval of the wireless device. Wireless device 704, which may have a length from between 1 cm to 10 cm, is entirely implanted into one chamber. Wireless device 704 may contain tines that secure the wireless device in place without suture. Wireless device 704 may contain suture ports for quick suturing of the device to the heart wall using a working instrument through the catheter channel.

Figure 8A:
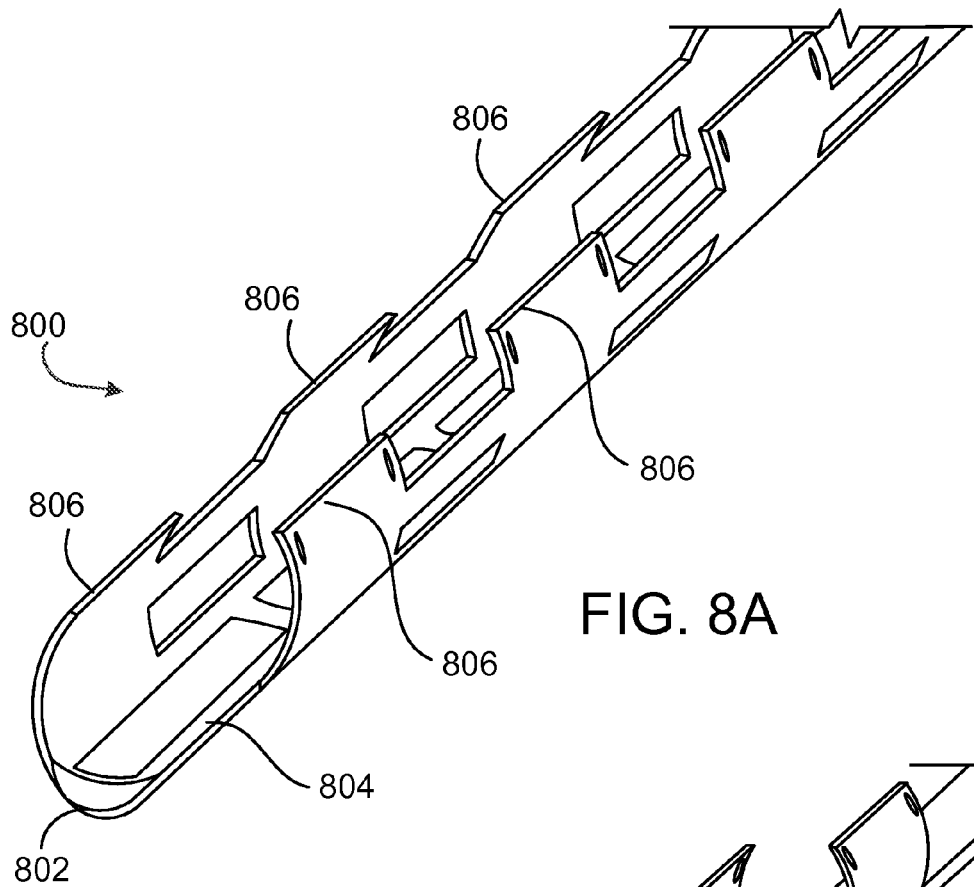
FIGS. 8A and 8B illustrate an example of a celiac cuff device.
Figure 8B:
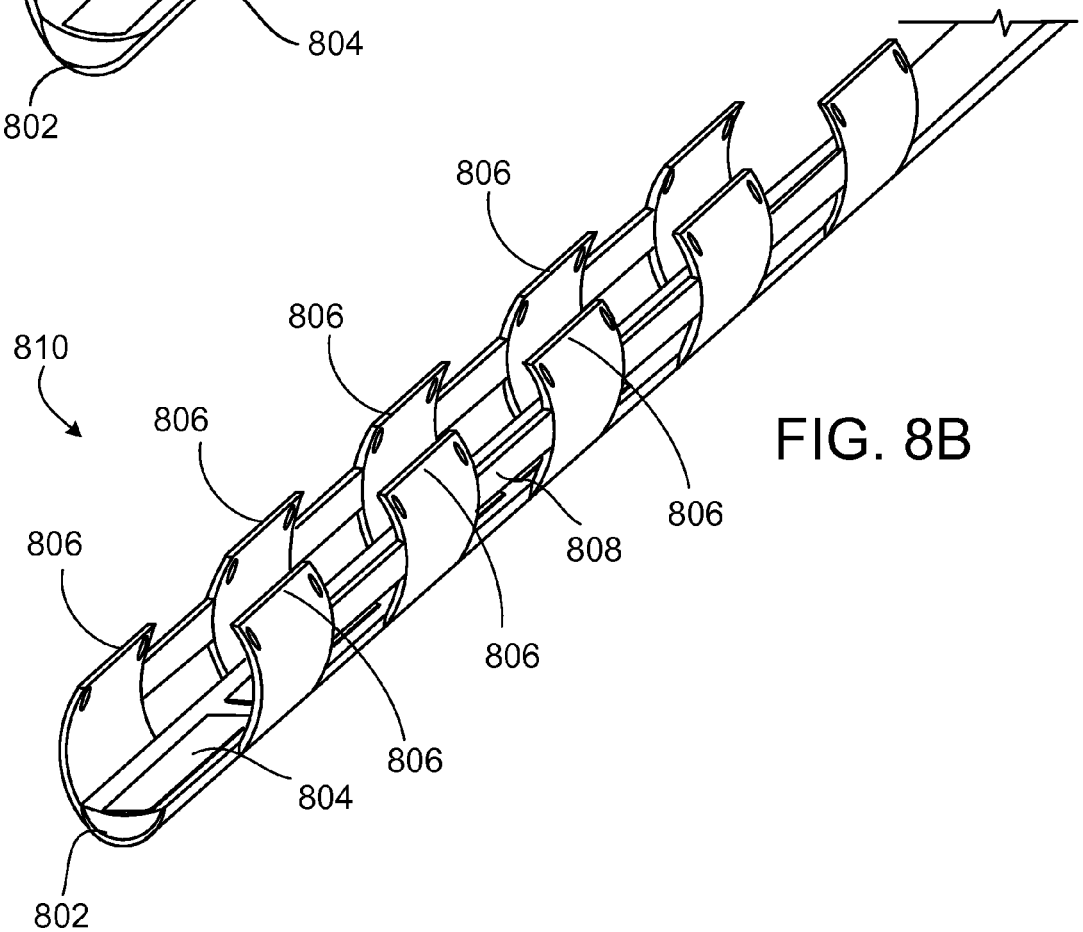

FIG. 8A illustrates an example wireless device in the configuration of a stimulating cuff device 800. The stimulating cuff device 800 includes distal end 802, electrodes 804, and suture arms 806.

The body of the stimulating cuff device 800 can be made of a soft insulation material such as polyurethane or silicone. The total length of stimulating cuff device 800 may be from between 5.0 mm and 600 mm. The stimulating cuff device body may be ideal for stimulating nerve bundles around cylindrical anatomical bodies like the celiac artery.

The stimulating cuff device 800 may include suture arms 806 that extend off of the electrode body to wrap the device around a nerve. The suture arms may extend from between about 1.0 mm and about 8.0 mm from the device body. The suture arms may have length from between about 5.0 mm and about 100 mm. The suture arms may have a curvature radius from between about 0 degrees and about 30 degrees. The suture arms may have a thickness from between about 0.1 mm and about 1.0 mm. The suture arms may have suture ports with diameter from between about 0.1 mm and about 0.5 mm. For example, a physician may anchor stimulating cuff device 800 to a surrounding tissue by applying suture to suturing arms 806 and the surrounding tissue.

Electrodes 804 may deliver stimulation unidirectional to the nerve tissue. Examples of electrode 804 can be from between about 0.5 mm to about 2.0 mm wide and about 1.0 mm to about 10 mm long. Examples of electrodes 804 may be made of a biocompatible metal such as platinum, platinum-iridium, or titanium nitride.

One or more electronic circuits may be located within the stimulating cuff device 800. The electronic circuits of stimulating cuff device 800 are not visible in FIG. 8A. However, FIG. 8B shows another example stimulating cuff device 810 with electronic circuits 808, electronic circuits 808 may be coupled to electrodes 804. Using internal antennas, stimulating cuff device 800 and 810 may receive electrical power for stimulation radiated from a wireless transmitter, as described above and below. The electronic circuit(s) may extract the electrical energy from the received input signal to provide power to the passive components and allow for stimulation of an excitable tissue. More examples of electrodes 804, the electronic circuitry, and the internal antennas, as well as the detailed description of a non-inductive power reception mechanism are presented below in association with FIGS. 10 to 20.

Figure 9A:
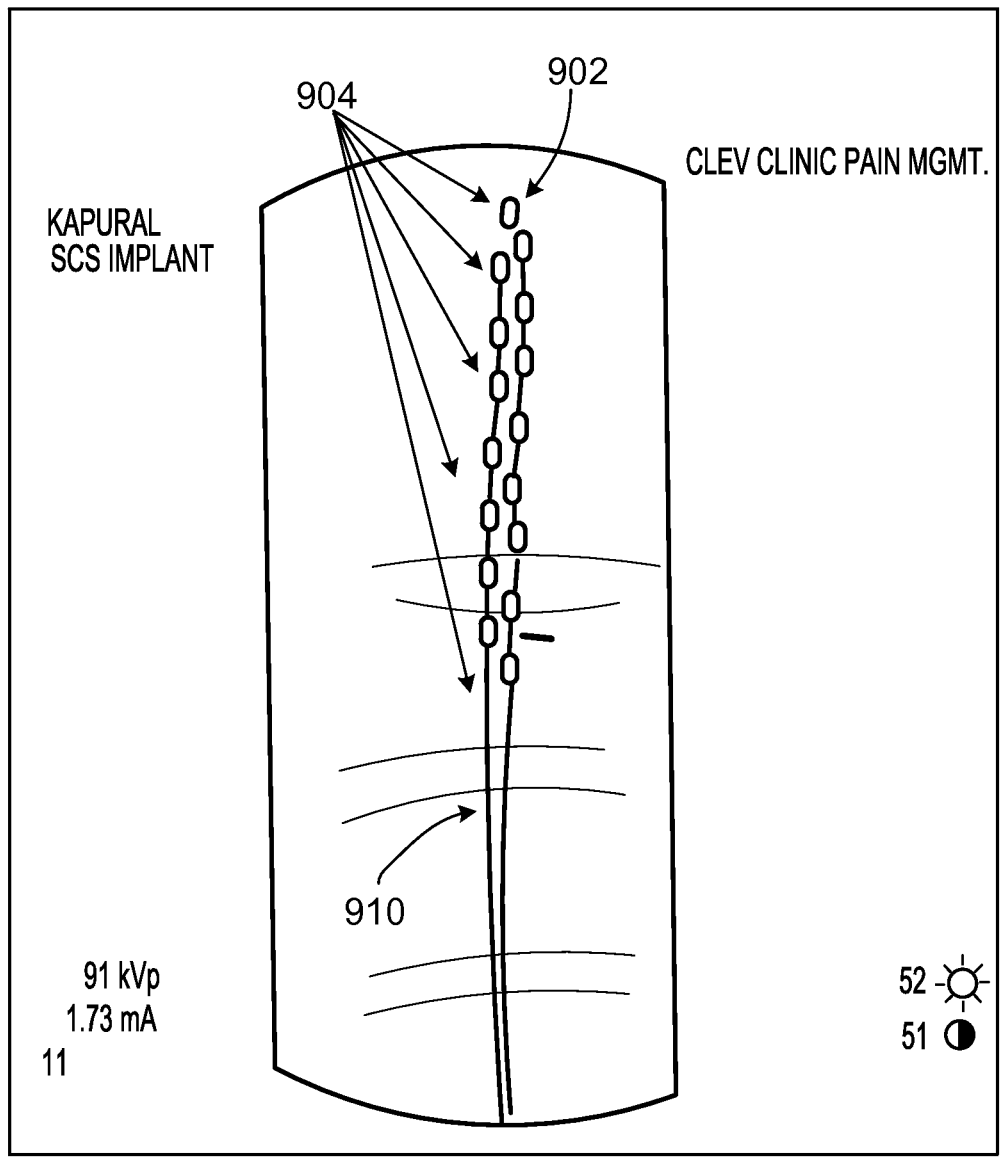
FIG. 9A illustrates the anatomical placement of devices in dorsal column spinal cord stimulation for abdominal pain therapy.
Figure 9B:
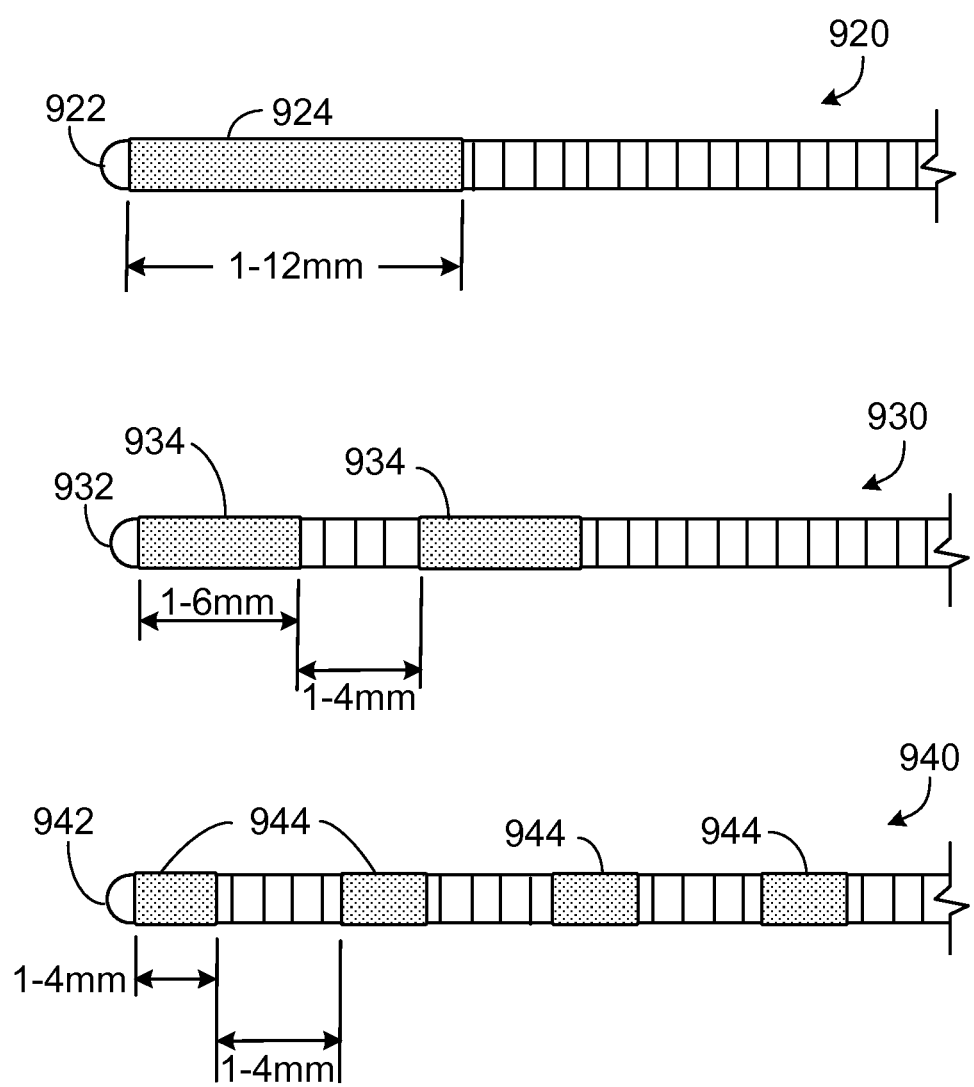
FIG. 9B illustrates the distal tip of an example device.

Referring now to FIGS. 9A and 9B, a system and method for spinal cord stimulation are described. Spinal cord stimulation (SCS) has been used to treat a variety of disorders, such as the treatment of chronic pain of neuropathic or ischemic origin (e.g., refractory angina), chronic abdominal pain, chronic visceral pain and the like. Various types of SCS leads have been used to provide therapeutic pain relief. These lead configurations often include cylindrical percutaneous leads and paddle lead form factors. Cylindrical percutaneous leads typically have diameters in the range of about 1.3 mm and contain a number of circular electrodes. Paddle leads contain electrodes with a greater surface area directionally targeted for control over the excitation of the nerve bundles. The spinal cord stimulator exerts pulses electrical signals to the spinal cord to control the pain symptoms. The stimulating devices are typically implanted in the epidural space and the electrical pulse generator and power supply are implanted tin the lower abdominal area or gluteal region, with conducting wires connecting the electrodes to the generator. Complications with SCS range from simple easily correctable problems to devastating paralysis, nerve injury and death. The most common complications include lead migration, lead breakage, and infection. Other complications include hematomas (subcutaneous or epidural), cerebrospinal fluid (CSF) leak, post dural puncture headache, discomfort at pulse generator site, seroma and transient paraplegia. Hardware-related complications such as electrode migration, fractured electrodes, and rotation of pulse generator are also reported.

Implementations disclosed herein may solve many of the problems with existing SCS techniques because the lead can be connected to the neurostimulator or controller wirelessly. The wireless coupling feature may obviate the most invasive and expensive portion of the implantation procedure; namely, the incision in the upper buttock or abdomen and the connection of the controller to the neurostimulator. In addition, this allows for a significantly smaller electrode lead, thereby reducing the invasiveness of the procedure and increasing the options for percutaneous delivery of the electrode lead.

Some implementations may include an implantable wireless device. The wireless device may contain one or more electrodes adapted for stimulation of the nerves, passive circuitry and an antenna for receiving an input signal. Further examples of wireless devices are presented below in association with FIGS. 10 to 20.

FIG. 9A illustrates the anatomical placement of two wireless devices 910 in dorsal column spinal cord stimulation (as shown on a X-Ray image). Electrodes 904 of each wireless device 910 are shown as radio-opaque marks. Distal ends 902 are also visible. As indicated by FIG. 9A, the placement of the device may be accomplished by the use of an introducer. The placement of the device may be guided by fluoroscopy, including X-Ray and ultrasound, to verify that the device has been placed in the correct position.

FIG. 9B illustrates three example wireless devices. Wireless device 920 may have one electrode 924 located close to distal tip 922. The length of electrode 924 may be about 12 mm. Wireless device 930 may include two electrodes 934 spaced apart and close to distal tip 932. Electrodes 934 may be about 6 mm in length and spaced apart by about 4 mm. Wireless device 940 may include four electrodes 944 spaced apart and close to distal tip 942. Electrodes 944 may be about 4 mm in length and spaced apart by about 4 mm.

During the surgical procedure, a wireless device may be advanced or delivered subcutaneously and positioned such that the electrodes are implanted on in the appropriate location in the epidural space of the patient's spinal cord. The example wireless device may communicate with an external controller to effectuate therapeutic effect.

The external controller may include electronic circuitry, a power source and a transmitting antenna. The external controller includes several predetermined programs that comprise combinations of pulse amplitude, pulse width, frequency, ON time and OFF time. The physician and/or patient may determine the particular program for therapy.

Once the program is determined, the external controller sends an input signal via a radio frequency carrier signal (as described above) to the antenna within the implantable wireless device. The internal antenna may receive the input signal. The internal circuitry on the wireless device then may convert the received input signal to electrical pulses. The electrical pulses may be applied to the electrodes within the wireless electrode lead to modulate the nerves of the spinal cord and treat the chronic pain.

Figure 10:
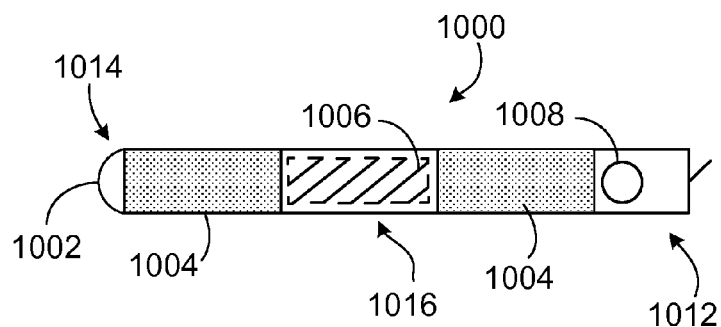
FIG. 10 illustrates an example of a miniature implantable device including wireless power receiving electronics.

FIG. 10 illustrates an example miniature implantable device 1000. The implantable device 1000 includes a body 1016 with a distal end 1014 and a proximal end 1012.

The distal end 1014 includes a rounded tip 1002. The distal end 1014 of the miniature wireless device body 1016 may include a non-conductive tip 1002 that is rounded with a length of between about 0.5 mm and about 1.0 mm, with a smooth finish for navigating the device through tissue.

The device body 1006 includes electrodes 1004 and houses electronic circuitry 1006. In some implementations, the miniature implantable device may have between one and twenty-four cylindrical electrodes 1004 on its distal end 1014 with a diameter between about 0.1 mm and about 0.8 mm for stimulation applications. The diameters and other sizes may, of course, vary from one target treatment to another target treatment. The electrodes 1004 may have a longitudinal length of between about 0.25 mm and about 6.0 mm from the distal end 1014 toward the proximal end 1012. The spacing between the electrode contacts may be between about 0.25 mm and about 6.0 mm. The total electrode surface area of the cylindrical wireless lead body may be between about 0.06 $mm^2$ and about 250.0 $mm^2$.

The proximal end 1012 includes a suturing feature 1008 and a mating feature 1010. The suturing feature 1008 is a passage through the proximal end with a central axis that is parallel to a longitudinal axis of the device body 1006. Suturing feature 1008 may allow a clinician to suture and anchor implantable device 1000 during an implantation procedure. For instance, suture can be passed through the passage of suturing feature 1008 and tied to tissue. In some cases, the implantable device 1000 can be sutured to the surrounding tissue. Suturing the implantable device may reduce mobility and improve stability of the implanted device.

Mating feature 1010 may allow the device 1000 to be mechanically mated with a stylet, as disclosed herein. In one configuration, mating feature 1010 is a concave indentation that extends along a longitudinal axis of the device body 1006 from the proximal end 1012. The concave indentation mates with a corresponding feature on a placement stylet or suction stylet. The concave stylet-mating feature on the proximal end 1010 of implantable device 1000 can have, for example, a length of between about 0.1 mm and 1.0 mm. In other configurations, the stylet-mating feature 1010 may be semi-spherical or asymmetrical in shape for improved steerability of the device during implantation.

The various devices described herein, including device 1000, may include, for example, anywhere from one to twenty-four electrodes 1004, any of which can be designated by a programmer user as either a cathode or an anode. For example, electrodes 1004 can include multiple cathodes coupled to the targeted tissue as well as at least one anode. The electrode array can receive electrical stimulation pulses ranging from about 0 to about 10 V peak amplitude at a pulse width up to about 1 millisecond. Such stimulation pulses may be from a single receiver element within the device body. The polarity of the electrodes can produce various volume conduction distributions from the cathodes to the anodes to inhibit or excite surrounding excitable tissue, which may include A-δ and/or primary or secondary c-fiber afferents. To reduce electrode impedance, the electrodes may be made of a conductive, corrosion resistant, biocompatible material such as, for example, platinum, platinum-iridium, gallium-nitride, titanium-nitride, or iridium-oxide.

The miniature implantable device 1000 may be 0.8 mm diameter or smaller. Miniature implantable device 1000 may receive microwave or RF energy from an external source non-inductively and without a wire. The miniature implantable 1000 device may contain the circuitry necessary to receive the pulse instructions from a source external to the body.

In particular, electronic circuitry 1006 of the miniature implantable device may convert an input signal received at the one or more antennas into an electrical energy and electrical pulses. In some implementations, extension tubing can provide an enclosure that houses, for example, flex circuitry. In some embodiments, the electronic circuitry 1006 may include one or a plurality of diodes that function to rectify the wireless signal, such as a sinusoidal signal, picked up by the non-inductive antenna(s). The diodes have a low threshold voltage to maximize the energy used for creating waveforms and power. Additionally, internal circuitry 1006 may include a charge balancing microelectronic component to reduce or prevent corrosion as well as a current limiter.

In certain embodiments, the electronic circuitry 1006 may include one or more non-inductive antennas, a rectifier, a charge balancer, a current limiter, a controller, and a device interface. In brief, the rectifier functions to rectify the signal received by the one or more non-inductive antennas. The rectified signal may provide power to electrodes 1004. The rectified signal may also be fed to a charge balance component that is configured to create one or more electrical pulses such that the one or more electrical pulses result in a substantially zero net charge (that is, the pulses are charge balanced). The charge balanced pulses are passed through the current limiter to the electrode interface, which applies the electrical pulses to electrodes 1004.

In some implementations, an internal dipole (or other) antenna configuration(s) may be used in lead 100 to receive RF power through electrical radiative coupling. This coupling mechanism can allow such devices to produce electrical currents capable of stimulating nerve bundles without a physical connection to an implantable pulse generator (IPG) or use of an inductive coil. In some implementations, between two to eight tissue-exposed-ring-antenna coupling contacts may be proximal to the electrodes. The tissue-exposed-ring-antenna coupling contacts may have a longitudinal length of between about 0.25 mm and about 6.0 mm from the distal end 1014 toward the proximal end 1010. The spacing between the tissue-exposed ring antenna coupling contacts may be between about 5 mm and about 80 mm. In certain implementations, tissue-exposed-small-antenna coupling contacts with a diameter between about 0.2 mm and about 0.6 mm may be used in lieu of the tissue-exposed-ring-antenna coupling contacts.

In some implementations, at least one of the antennas can be constructed as a conductive trace feature contained on one of the circuits. In other implementations, at least one of the antennas can be fabricated as a conductive wire connected to one of the circuits. In various implementations, implantable device 1000 my employ non-inductive, for example, dipole or other antenna configuration(s), to receive RF power through electrical radiative coupling.

For context, neural stimulating devices may utilize a battery-powered or charge-storage component. Such devices are no longer functional once the battery cannot be recharged or charge cannot be stored. Consequently, for an implanted device, a patient would need to undergo a subsequent surgical procedure to obtain a functional replacement device.

In contrast, some implementations disclosed herein do not rely upon battery power or charge storage for operation. In some configurations, the implantable device can receive electrical power from radiated RF energy non-inductively and without a wired connection. As a result, the life of an implanted device is no longer limited by the life of the battery or ability to store charge.

Further, the electrical radiative coupling mechanism (for example, a dipole antenna) can be utilized to improve the form factor of the miniature implanted device and allow for miniature diameters. Electrical radiative coupling may also allow for the transmission and reception of energy at greater depths with less degradation in efficiency than inductive coil techniques. This electrical radiative coupling can provide an advantage over devices that employ inductive coupling where the efficiency of such implants may be highly dependent on the distance separating the external transmitter coil and the implanted receiver coil.

Accordingly, some implementations disclosed herein do not include inductive loops to receive RF energies in a wireless manner. Instead, some implementations disclosed herein use electric radiative coupling to receive RF energies. Such implementations facilitate a smaller form factor for a fully functional implantable electrical stimulation or recording device. The improved form factor may result in a less invasive surgical procedure for placement of the device. The improved form factor may also decrease scarring the amount of bodily tissue in contact with the implanted device is reduced.

A telemetry signal may be transmitted by the miniature implantable device 100 to deliver information to an external controller. The telemetry signal may be sent by modulation of a carrier signal. The telemetry signal does not interfere with the input received to power the miniature implantable device. In one example, the telemetry signal and powering signal are combined into one signal, where the RF telemetry signal is used to modulate the RF powering signal, and thus the implanted device is powered directly by the received telemetry signal; separate electronic subsystems harness the power contained in the signal and interpret the data content of the signal. In other embodiments, the telemetry output rate is at least 8 kilobits per second.

In other implementations, a RF pulse generator system, located externally to the miniature implanted device 1000, may store parameters defining the excitation pulses to be applied at electrodes 1004, which are transmitted via the second antenna.

Figure 11:
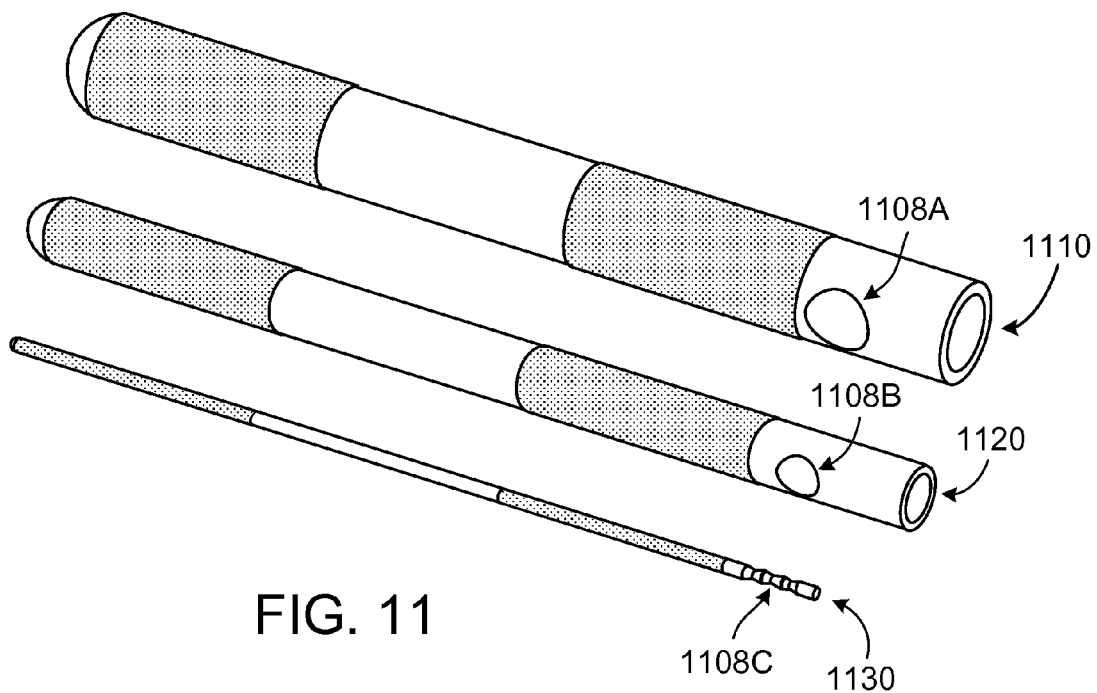
FIG. 11 shows three different sized miniature implantable devices.

FIG. 11 illustrates three examples of miniature implantable devices 1100A, 1100B, and 1100C with various diameters. Miniature implantable device 1100A is a miniature implantable device with a diameter of 0.8 mm. Miniature implantable device 1100A includes a suturing feature 1108A to allow a clinician to suture and anchor implantable miniature implantable device 1100A during an implantation procedure. For instance, suture can be passed through the passage of suturing feature 1108A and tied to tissue such that the mobility of the implanted device is reduced. As illustrated, implantable device 1100A also includes an indentation 1110A on the proximal end to allow for mating with a placement stylet during implantation.

Miniature implantable device 1100B has a diameter of 0.4 mm and has a suturing feature 1108B similar to 1108A. Implantable device 1100B also includes an indentation 1110B on the proximal end to allow for mating with a placement stylet during implantation.

Miniature implantable device 1100C has a diameter of 0.1 mm. Miniature implantable device 1100C includes a suturing feature 1108C in the form of ribs to aid suture in attaching to a surrounding tissue Implantable device 1100C also may include an indentation 1110C to allow for mating with a placement stylet during implantation.

Figure 12:
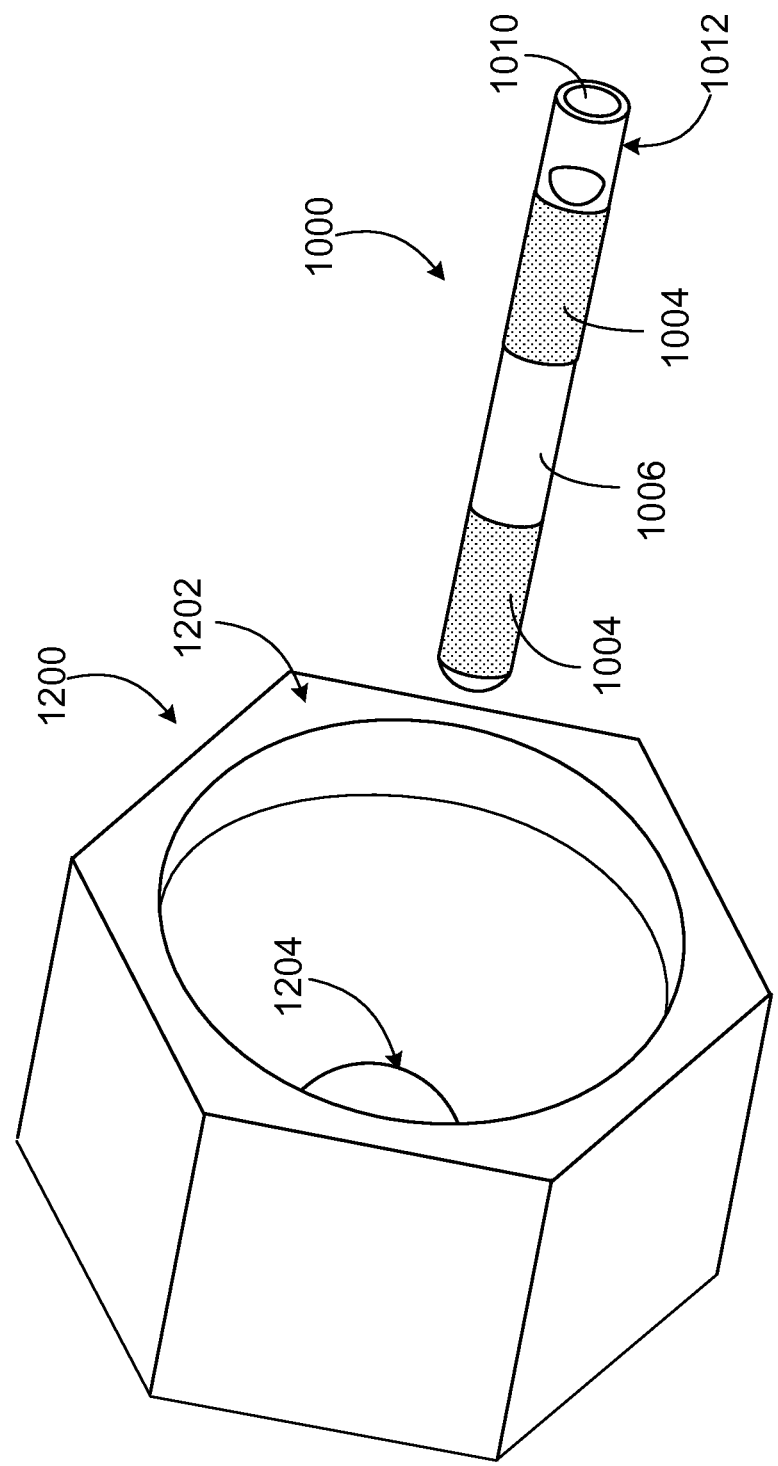
FIG. 12 illustrates a miniature implantable device entering an introducer needle.

FIG. 12 illustrates the miniature wireless device 1000 (e.g., a 0.8 mm diameter) entering an 18 gauge needle 1200. The distal end (not shown) of miniature implantable device is in position to enter the proximal opening 1202 of an 18-gauge needle 1200. Miniature implantable device 1200 has a diameter small enough to fit into the inner lumen 1204 of the needle 1200. The illustration may correspond to an implantation of a miniature implantable device with a diameter of 0.8 mm, shown as the implantable device 1100A in FIG. 11. Notably, the middle and bottom devices (0.4 mm and 0.1 mm, respectively) shown in FIG. 11 are sized for advancement through introducer needles with even smaller sizes, (e.g., 22 gauge or smaller).

While it is possible to place the device 1000 directly into an introducer needle, doing so may not be desirable as the implantable device enclosure may not be as rigid as a guide wire and may not slide easily within the inner lumen of the introducer needle. Yet, a guide wire may not be used because the implantable device may not have a central void through which to mount the guide wire. To improve the ease of placement through an introducer needle, a stylet may be used to provide some rigidity to the miniature device.

Figure 13A:
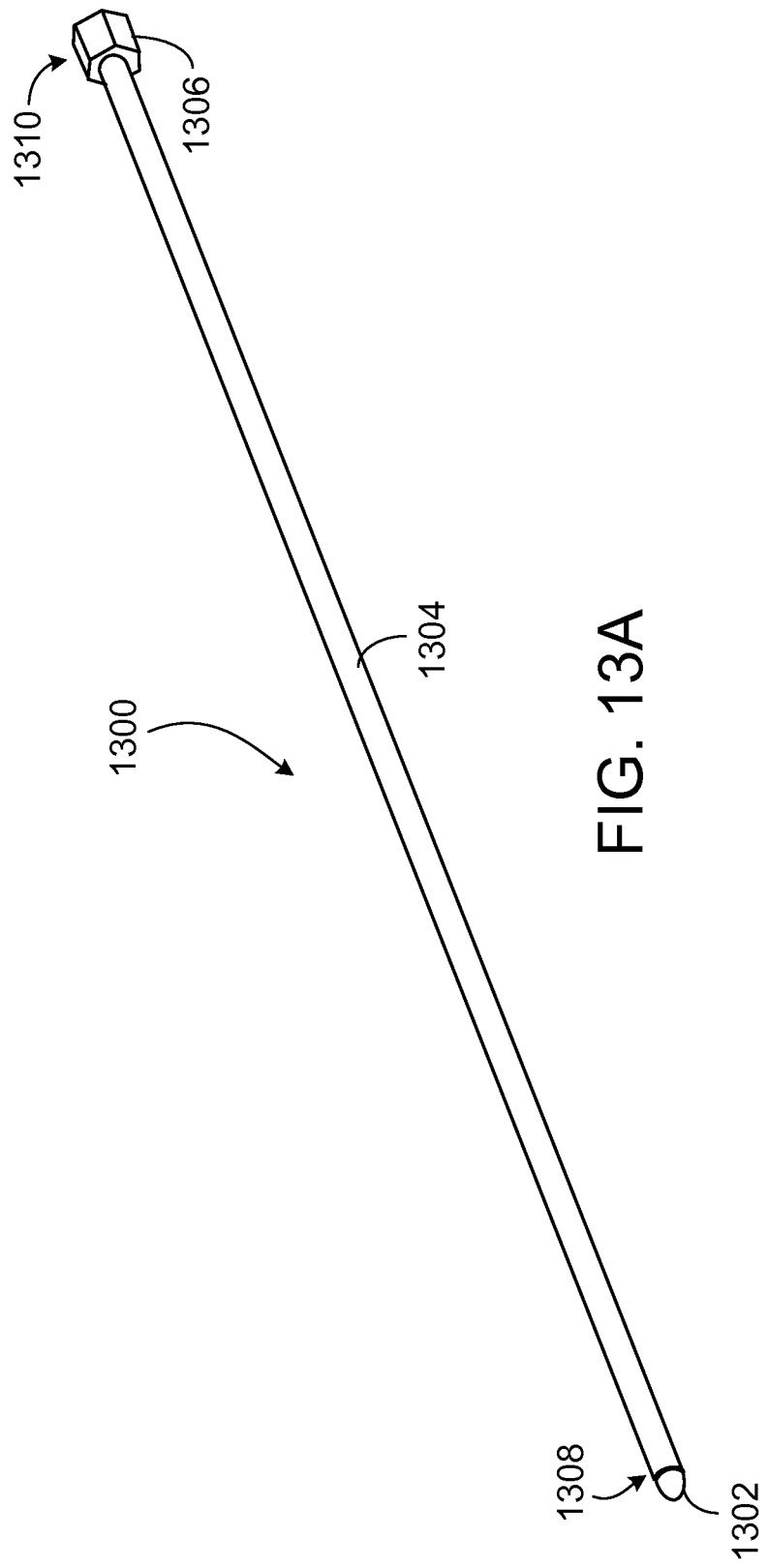
FIG. 13A shows a placement stylet capable of mating with a miniature implantable device.

FIG. 13A shows a placement stylet 1300 capable of mating with a miniature implantable device 1000 according to some implementations. Placement stylet 1300 includes a distal end 1308, device body 1304, and proximal end 1310. Distal end 1308 includes a mating feature 1302 to allow the placement stylet 1300 to engage, for example, miniature implantable device 1000. The mating feature 1302 is, for example, a convex protrusion that is shaped and sized to mate with the concave indentation 1010 of the lead 1000. Proximal end 1306 includes handle 1306 for operator to hold placement stylet 1300, for example, during an implantation procedure. Placement stylet 1300 can have a longitudinal length of between about 50 mm and about 177 mm. Placement stylet 1300 can have an outer diameter in the range from between about 0.1 mm and about 0.9 mm. Placement stylet 1300 may be made of a rigid biocompatible material such as stainless steel, titanium, nylon, or polyethylene.

Figure 13B:
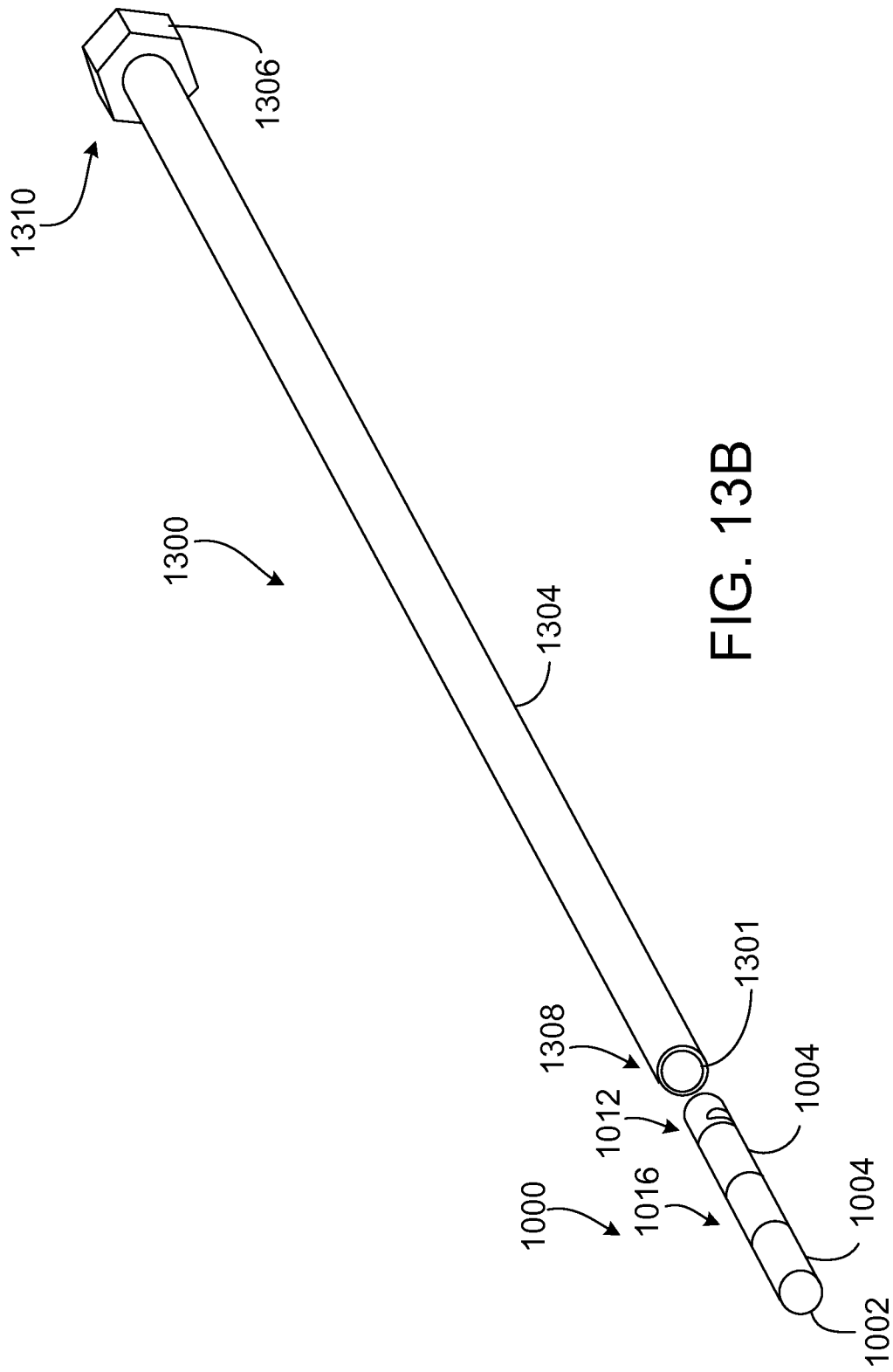
FIG. 13B illustrates a miniature implantable device mated with a placement stylet.

FIG. 13B illustrates a miniature implantable device 1000 mated with a placement stylet 1300. A clinician may mate the miniature implantable device 1000 onto the placement stylet 1300. The mating feature 1302 on the distal end 1308 of the stylet may mate with mating feature 1010 on the proximal end 1012 of miniature implantable device 1000. Mating feature 1302 on placement stylet 1300 may be semi-spherical in shape, and may provide mechanical gripping for placement stylet 1300 to engage the miniature implantable device 1000 during placement. Mating feature 1302 may be complementary in shape to the shape of mating feature 1012 on the proximal end 1010 of the device 1000. In some configurations, mating feature 1302 may be convex in shape. In other configurations, mating feature 1302 may include extruded shapes for mating the stylet 1200 to the miniature implantable device 1300 at mating feature 1012, which may have a square, hexagon, star, or an asymmetrical shape. Mating feature 1302 may only protrude from the distal end 1308 of placement stylet 1300 from between 0.1 mm and 1.0 mm and may not fill the entirety of the device body 1006 (that is, the feature 1302 may only extend partially into device body 1006). Mating feature 1302 may have a surface material that allows for increased friction to improve the mate between placement stylet 1300 and the miniature implantable device 1000. Example materials may include silicon or polyurethane.

Figure 14A:
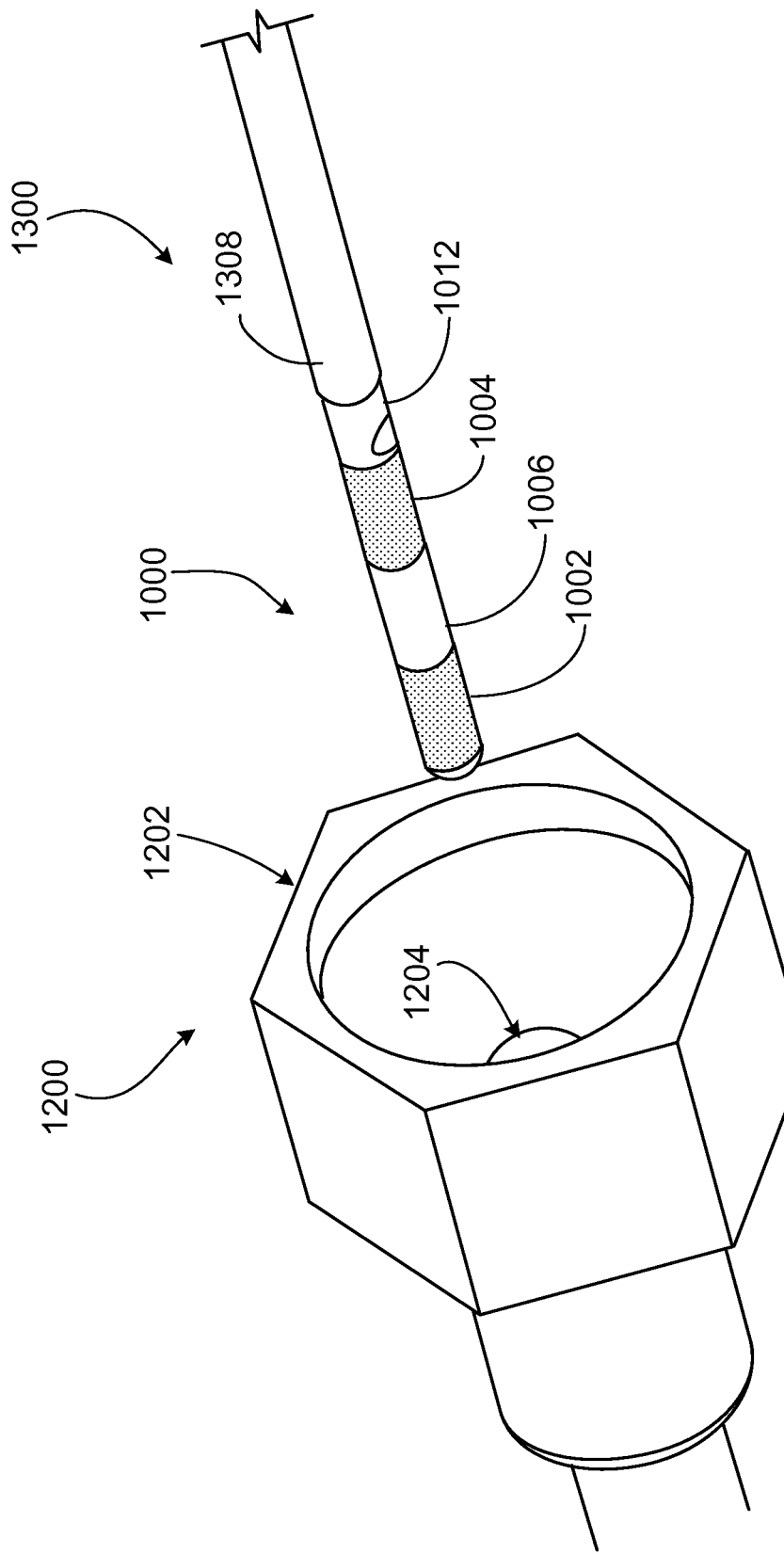
FIG. 14A shows a miniature implantable device mated with a placement stylet entering a proximal opening of an introducer needle.

FIG. 14A illustrates a miniature implantable device 1000 mated with a placement stylet 1300 entering a proximal opening 1202 of needle 1200. Miniature implantable device 1000 includes lead body 1016 that includes electrodes 1004 and houses electronic circuitry 1006. The proximal end 1012 of miniature implantable device 1000 is now mated with the distal end 1308 of placement stylet 1300. As illustrated, after the miniature implantable device 1000 has been mated to placement stylet 1300, the subassembly of the device 1000 with the stylet 1300 can now be inserted into an 18 gauge needle 1200 or smaller. In particular, the miniature implantable device 1000 at the proximal opening 1202 of needle 1200 is being pushed into position with the placement stylet 1300. In fact, the stylet/miniature device subassembly may now slide freely within the inner lumen 1204 of the needle 1200. The free sliding motion may aid in the surgical placement of the miniature device 1000.

Figure 14B:
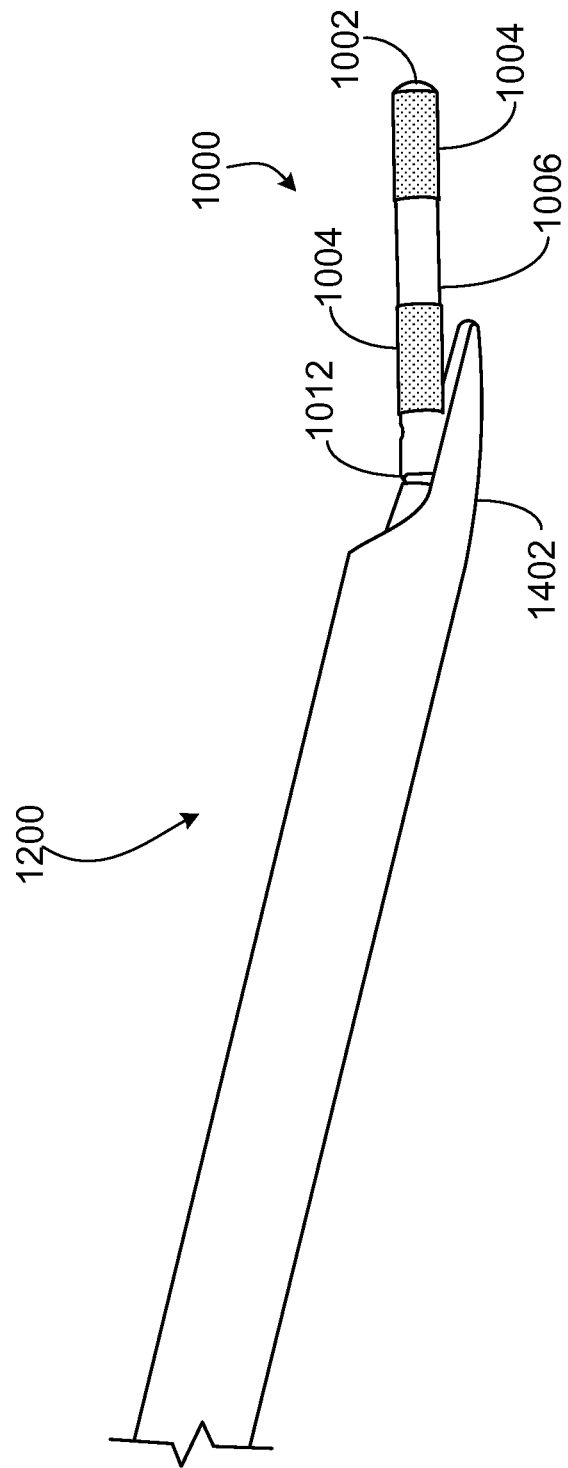
FIGS. 14B and 14C show a miniature implantable device mated with a placement stylet exiting a distal tip of an introducer needle.
Figure 14C:
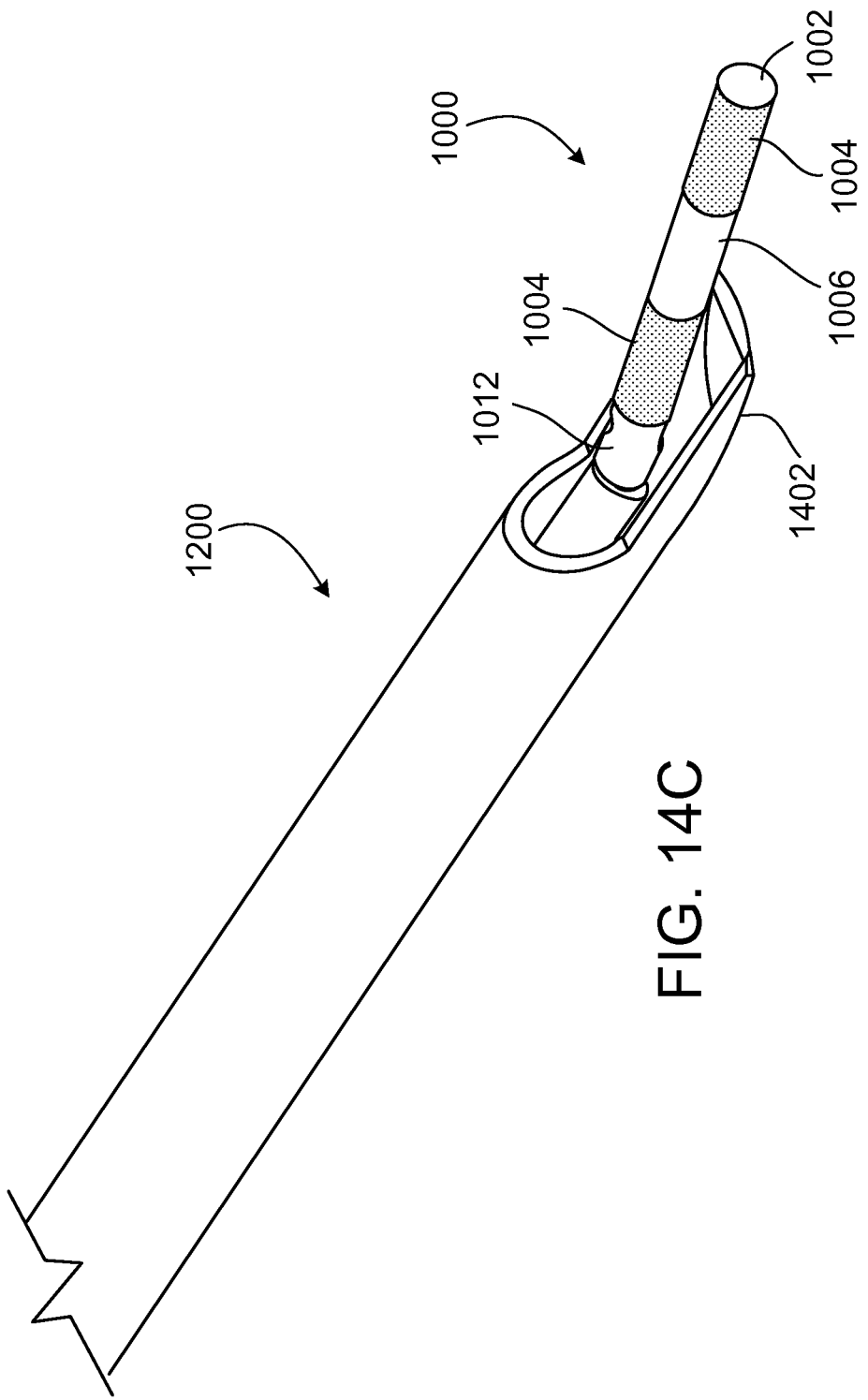

FIGS. 14B and 14C show a miniature implantable device 1000 mated with a placement stylet 1300 exiting a distal end 1202 of needle 1200. As discussed above, the miniature implantable device 1000 may freely traverse the inner lumen 1204 of needle 1200 with a size of 18 gauge or smaller. Once the traversal is completed, the miniature implantable device 1000 may exit the needle under the pushing force applied on the placement stylet 1300 mated to the device 1000. As illustrated, rounded tip 1002 and body 1016 of miniature implantable 1000 have exited the distal end 1402 of needle 1200. The portions of body 1016 that include electrodes 1004 and electronic circuitry 1006 are also shown on FIGS. 14B-14C. The proximal end 1012 of miniature implantable 1000 is mated to the distal end 1308 of placement stylet 1300. After the implantable 1000 has been placed into a target region, the implantable device 1000 may be sutured or anchored in place. Thereafter, the placement stylet 1300 may be unmated from the implanted 1000. A clinician may then withdraw the placement stylet 1300 by pulling the placement stylet 1300 out of the patient's body through the needle 1200. The placement and withdrawal process may be performed under imaging guidance, such as, for example, X-Ray fluoroscopy, ultrasound fluoroscopy, etc. Once the procedure is completed, needle 1200 may be removed.

Figure 15:
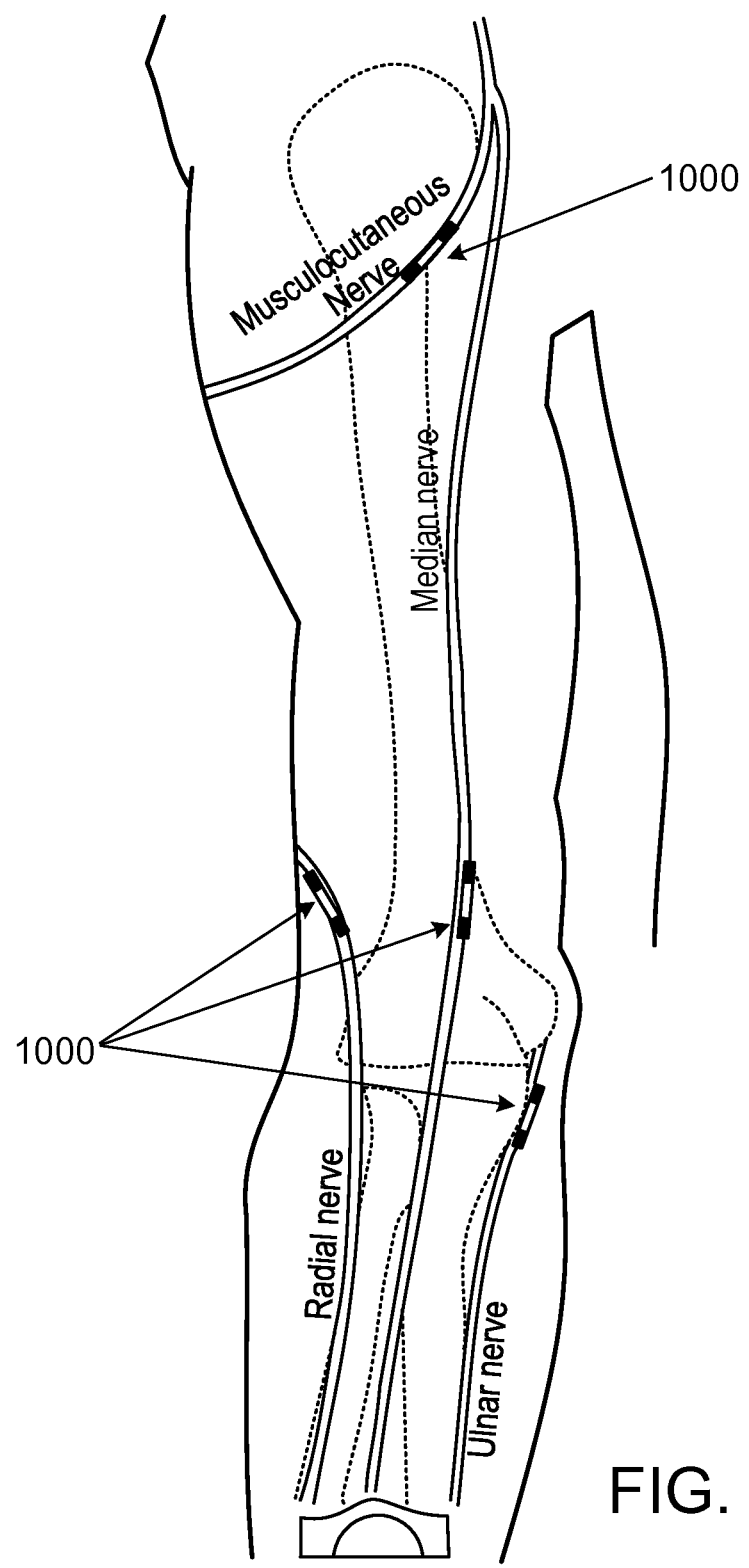
FIG. 15 illustrates the anatomical placement of four miniature implantable devices in the forearm.

FIG. 15 demonstrates the feasibility of placing multiple miniature implantable devices in the anatomical positions of the forearm. The compact size of the miniature implantable device 1000 may allow minimally invasive placement procedure, thereby reducing complications during procedure and improving recovery time after procedure. Moreover, the compact size may allow multiple miniature implantable devices to be placed in nearby target areas. As shown in FIG. 15, four miniature implantable devices 1000 are placed into the forearm of a patient, one in the upper forearm area and three in the lower forearm area. Each implanted lead may treat a specific nerve branch in the forearm region. Similarly, the miniature implantable devices 1000 also may be delivered to treat a neural tissue branching from the spinal column including but not limited to the dorsal root ganglia, traversing, or exiting nerve. The miniature implantable devices 1000 may also be delivered to treat peripheral nerve targets such as the radius, ulnar, sciatic, femoral, occipital, or brachial nerves. Given the compact size of the miniature leads, two or more such devices may be placed with pinpoint precision to treat multiple nerve branches or peripheral nerve targets at the same time. In particular, two or more such devices may be placed with close proximity within a target area to provide pain-relief therapy to one or more excitable tissues within the target area. For instance, a patient may have one miniature implantable device 1000 implanted adjacent to or near a target area. If more therapeutic effect is desired, the patient may have additional miniature implantable devices 1000 implanted adjacent to or near the target area to enhance the therapeutic effect.

Figure 16C:
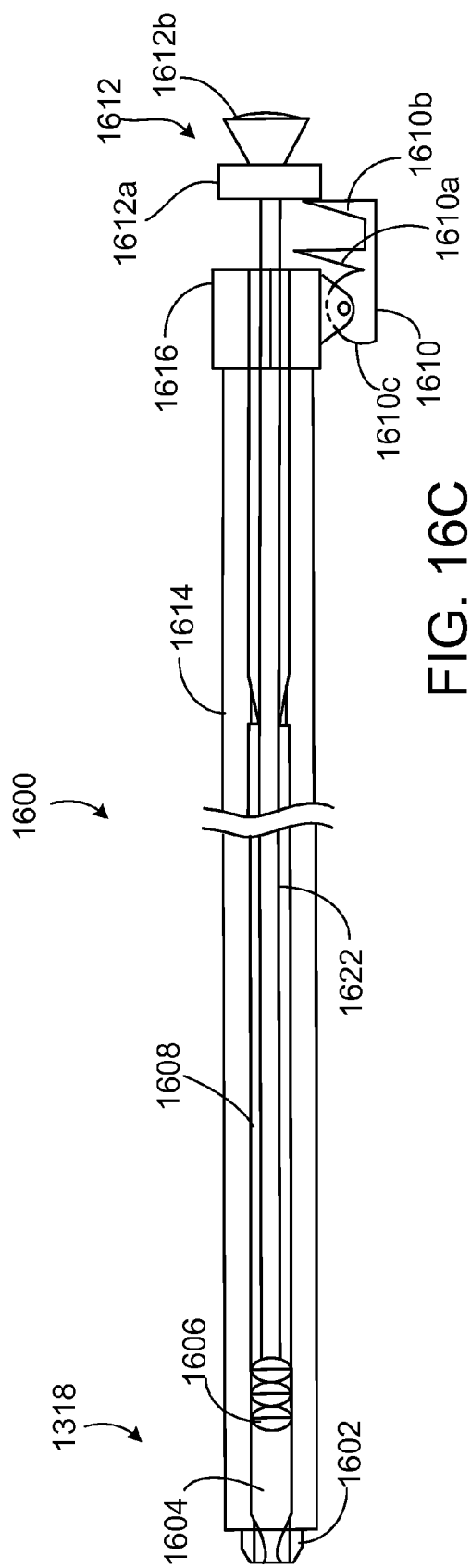
FIG. 16C illustrates the example suction stylet in second level of negative pressure mode.

FIGS. 16A-16E illustrate a suction stylet 1600 in various modes of operation. The suction stylet 1600 is different from the placement stylet 1000 described above. As shown in FIG. 16A, the suction stylet 1600 is hollow inside and may have an outer diameter of between about 0.1 mm and 0.9 mm and may have a longitudinal length of between about 50 mm and 170 mm. The suction stylet 1600 may have an inner diameter between about 0.05 mm and 0.75 mm. The suction stylet 1600 includes distal end 1618, stylet body 1614, and proximal end 1616.

The distal end 1618 may include a mating feature 1602, chamber 1604, and plunger tip 1606. Mating feature 1602 also may be referred to as the suction tip. In some configurations, mating feature 1602 may be semi-spherical in shape and may have a diameter between about 0.05 mm and 0.08 mm. Mating feature 1602 on suction stylet 1600 may mate to mating feature 1010 on miniature wireless lead 1000, in a manner similar to the mechanical mating described above. In some instances, a mating force may be provided by a negative air pressure created inside air chamber 1604 on suction stylet 1600. In particular, by moving the plunger tip 1606 along the shaft for inner plunger 1608, a negative air pressure may be created in chamber 1604.

Stylet body 1614 may include inner plunger 1608 located inside shaft 1622. The inner plunger shaft 1622 may have a diameter between about 0.05 mm and 0.75 mm, allowing the plunger 1608 to slide inside of the hollow suction stylet 1600. The total length of the inner plunger including the inner plunger handle may be between about 50 mm and 170 mm. The inner plunger shaft, when installed, may not protrude beyond the suction tip.

The proximal end 1620 of suction stylet 1600 may include base 1616, handle 1612, and locking feature 1610. Base 1616 may have a diameter of between about 0.1 mm and 0.9 mm depending on the outer diameter of the hollow stylet 1600 being utilized. Handle 1612 may include cap 1612a and tip 1612b. Cap 1612a closes the tubing of suction stylet 1600. Handle tip 1612b may be pulled Out during a placement procedure. The pulling may cause sliding motion of the plunger 1608 inside shaft 1622, which creates a negative air pressure in chamber 1604. Suction force may be created on suction tip, mating feature 1602, so that suction stylet 1600 is mated with miniature implantable device 1000. Locking mechanism 1610 may include spike 1610a, spike 1610b, and hinge 1610c. Hinge 1610c is mounted on base 1616 and may rotate to engage spikes 1610a and 1610b with cap 1612a, as discussed below.

FIGS. 16A to 16C show the suction stylet without the mating miniature implantable device. As illustrated, the inner plunger 1608 may be slid in a translating motion inside shaft 1622 to different locations within the hollow stylet 1600. Locking mechanism 1610 may be used to lock plunger 1608 into certain positions.

In particular, FIG. 16A shows the inner plunger 1608 in a complete seated condition with respect to the distal end 1620 of stylet 1600. In this position, no pressure differential may exist between the mating feature 1602 and plunger tip 1606.

Figure 16D:
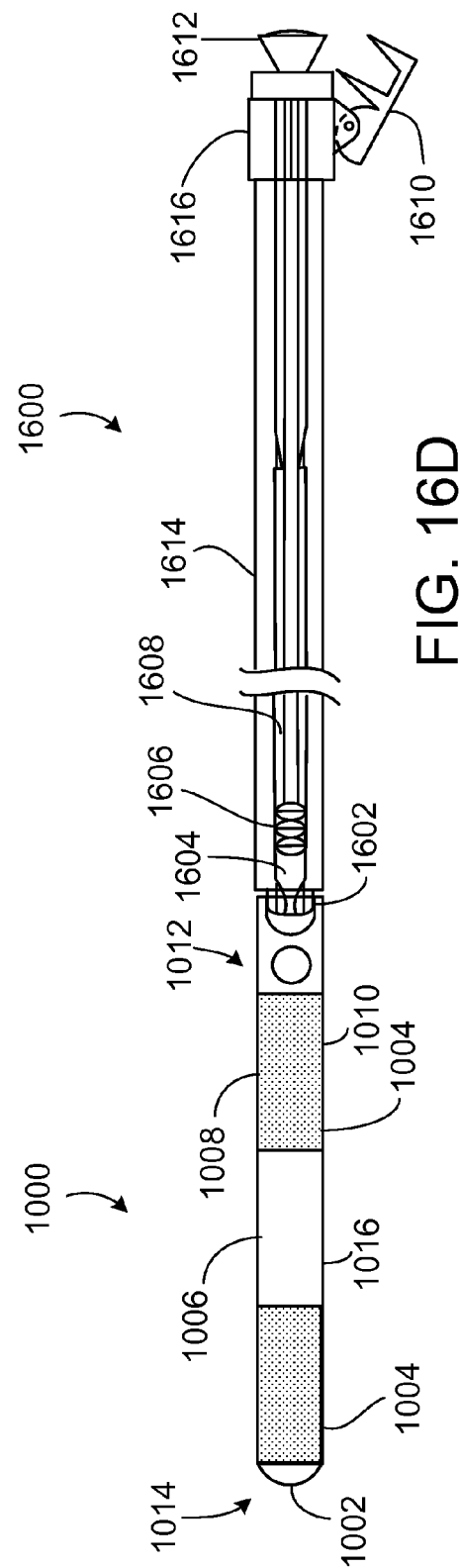
FIG. 16D illustrates an example miniature implantable device when the suction stylet is not active.

FIGS. 16B and 16D show the inner plunger 1608 at stage 1 position, which may be between about 1 mm and 10 mm from mating feature 1602 (suction tip) of the hollow stylet 1600. FIG. 16B shows suction stylet 1600 without the mated miniature implantable device 1000, while FIG. 16D shows suction stylet 1600 mated with miniature implantable device 1000. By pulling the handle tip 1612b away from the hollow stylet, a pressure differential may be generated to create a temporary mate between the miniature implantable device 1000 and the stylet 1600. The mate is between mating feature 1002 on miniature implantable device 1000 and suction tip 1602 on suction stylet 1600. Locking mechanism 1610, as shown in FIG. 16B, may lock the inner plunger 1608 in place by engaging spike 1610a between base 1616 and cap 1612a. Once locked, the pressure differential between suction tip (mating feature 1602) and plunger tip 1606 may be maintained. This locking mechanism may be adjustable to allow for the inner plunger to be locked in a desired location.

Figure 16E:
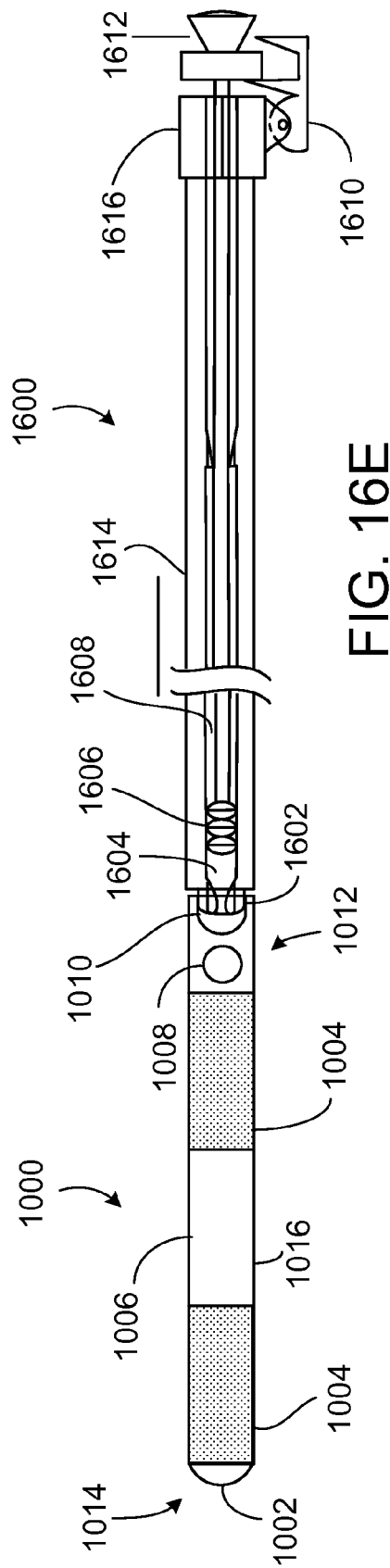
FIG. 16E illustrates an example miniature implantable device when the suction stylet is active.

FIGS. 16C and 16E illustrate the inner plunger 1608 being locked into a stage 2 location, which may be between about 2 mm and 30 mm from mating feature 1602 (suction tip) of the hollow stylet 1600. FIG. 16C shows suction stylet 1600 without the mated miniature implantable device 1000, while FIG. 16E shows suction stylet 1600 mated with miniature implantable device 1000. This stage may have a greater pressure differential generated than the stage 1 location depicted in FIG. 16B. In other examples, a suction stylet assembly may have one more locking stages depending on the locking mechanism utilized. An adjustable locking mechanism may allow for infinite locking distance locations.

The suction stylet design may provide the clinician the ability to install and remove the miniature implantable device 1000 from a patient. As discussed above, once suction stylet 1600 is activated to engage miniature implantable device 1000, an assembly of miniature implantable device 1000 and suction stylet 1600 may be created. The clinician may push the suction stylet to advance the entire assembly, for example, down the inner lumen 1204 of needle

1200, towards the target site. If the miniature implantable device 1000 is already implanted, the clinician can mate the miniature implantable device 1000 to the suction tip of the stylet 1600, then pull on handle tip 1612*b*. Plunger 1608 may slide inside shaft 1622, thereby creating a pressure differential between suction tip 1602 and plunger tip 1606. The pressure differential may engage the miniature implantable device 1000, and the clinician may withdraw the suction stylet 1600 to take the implanted lead 600 from within the patient.

Figure 17A:
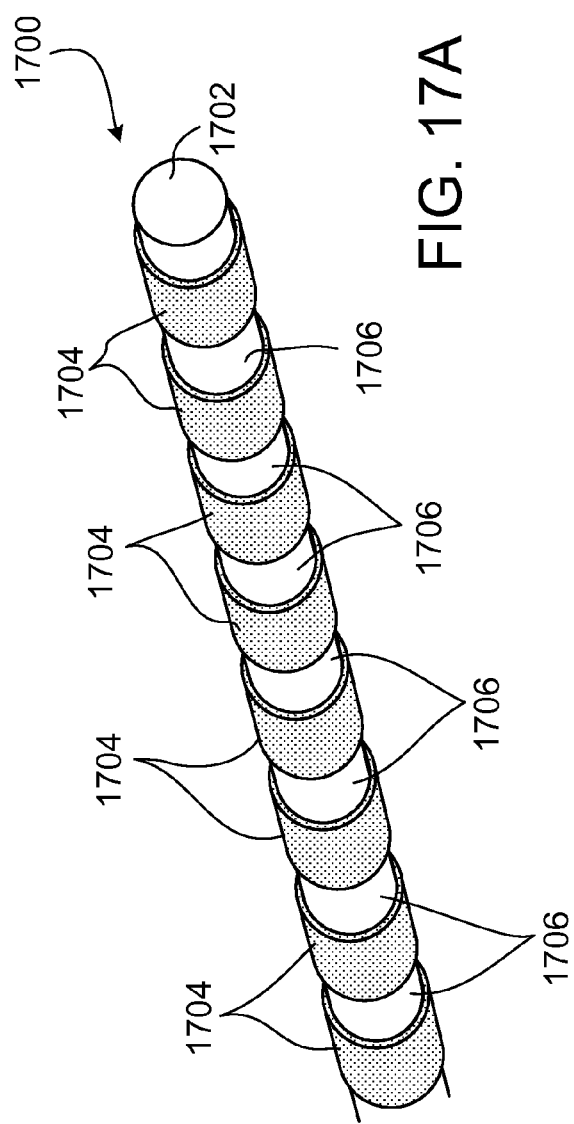
FIG. 17A illustrates a miniature implantable device with multiple recording or stimulating cylindrical electrode pads (eight shown).

FIG. 17A shows cylindrical electrodes 1704 (eight (8) shown) on the outside of a lead 1700. The outer diameter of lead 1700 may be 0.8 cm or smaller. Each cylindrical electrode 1704 may operate as a recording or stimulating electrode. A stimulating electrode may apply electric pulses to an excitable tissue to achieve therapeutic effect. A recording electrode may record or sense neural activity from surrounding tissue. In some instances, the electrodes may alternate between stimulating and recording electrodes. In the example shown, the miniature lead 1700 is not tethered and not connected to another structure or device for mechanical or electrical interface. One or more electrical flex circuitry may be internal to the miniature lead. The flex circuit may be inside gaps 1706, in between electrodes 1704. Lead 1700 may also include a rounded-tip 1702 for easy placement, as well as a mating feature to mate the lead 1700 with a stylet, such as those described above.

Figure 17B:
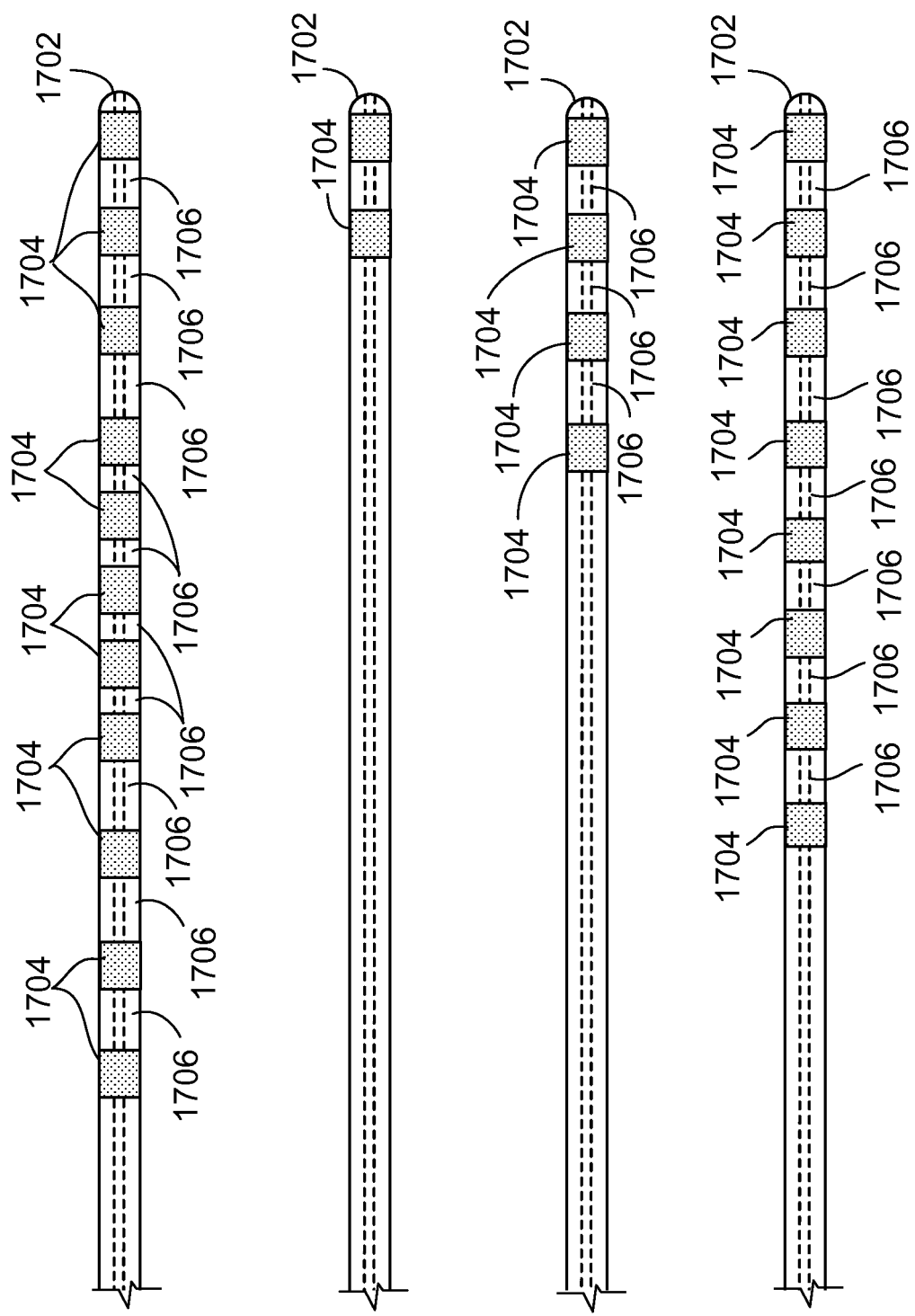
FIG. 17B illustrates various electrode configurations for stimulation and or recording electrodes on the miniature implantable device body, with various inter-electrode spacing options and mixture of recording and stimulation electrode assignments.

FIG. 17B shows four example miniature implantable devices incorporating multiple recording and/or stimulating electrodes 1704. The four example leads shown do not have an inner stylet lumen to mount a stylet or a guide wire, but may include a mating feature such as those described above. The recording and/or stimulating electrode pads 1704 may couple to a surrounding tissue for recording and/or stimulating. In a recording mode, neural activities of the surrounding tissue may be sensed and capture in electrical signals that encode such neural activities. In a stimulating mode, electric pulses may be applied to the surrounding tissue for pain relief. In some configurations, the electric circuitry may be spaced in between the recording and/or stimulating electrode pads, for example, in gaps 1706. As illustrated, example miniature implantable devices 1700 may include rounded tip 1702 for easy placement.

Figure 17C:
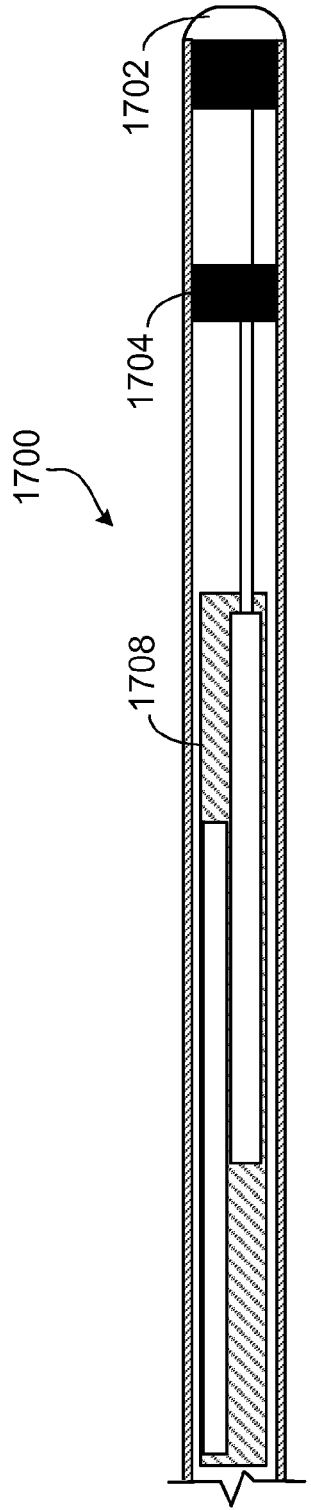
FIG. 17C is a cutout view of a miniature implantable device with stimulation or recording electrodes and the electronic circuitry and wireless power receiver.

FIG. 17C illustrates a miniature implantable device 1700 with stimulating and/or recording electrodes 1704 located at the distal end of the lead, in the direction of the rounded tip 1702. As illustrated, the electronic circuitry 1708 is located towards the proximal end of implantable device 1700, rather than spaced between the electrodes 1702.

For the configurations shown in FIGS. 17A to 17C, the electronic circuitry may provide power to drive the stimulating and/or recording electrodes. As described above, the electric pulses may be created by the electronic circuitry based on the input signal received at the antennas on the implantable devices. The electric pulses may be sent to a stimulating electrode to delivery pain-relief to an excitable tissue. As discussed above, a recording electrode may record neural activities of a surrounding tissue. The electronic circuitry also may route the recorded analog signal to the antennas on the implantable device which may in turn transmit the recorded analog signal to an external controller, located outside the patient body. In some implementations, the recorded analog signal may be processed and transmitted in a manner similar to the telemetry signal described above. For example, the transmission of the recorded analog signal, like the telemetry signal discussed herein, may be powered by the electrical power in the input signal.

Figure 18:
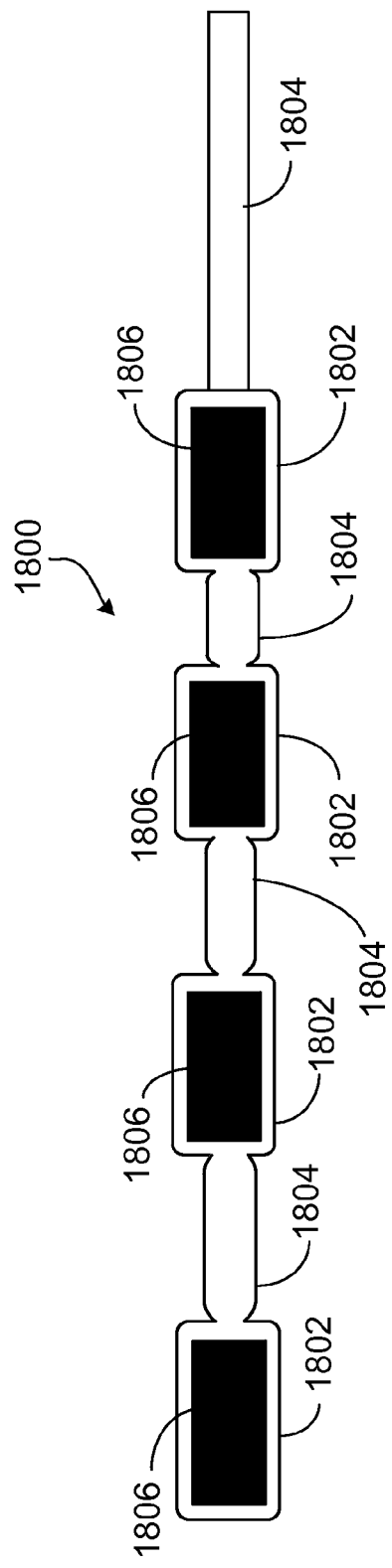
FIG. 18 illustrates a view of a miniature implantable device and a plate electrode configuration for the stimulation or recording pads.

FIG. 18 depicts an example of a lead 1800 with each electrode pad 1802 configured as a rectangular square. As illustrated, each rectangular square electrode pad 1802 may include an electrode 1806. Electronic circuitry may be located on structures 1804. Electrode 1806 may have a surface area of at least 0.06 mm2. This implantable device 1800 may have a total width from between about 0.5 mm and 0.8 mm. The height of the implantable device 1800 may be from between about 0.1 mm and about 0.8 mm. The total length of the implantable device 1800 may be from between about 10 mm and about 600 mm. The rectangular electrode pads 1502 may have a length from between about 0.5 mm and about 6.0 mm and a width from between about 0.45 mm and about 0.75 mm. The inter-electrode spacing may be from between about 0.1 mm and about 6.0 mm. This implantable device 1800 may be suitable for stimulating a relatively large area.

Figure 19:
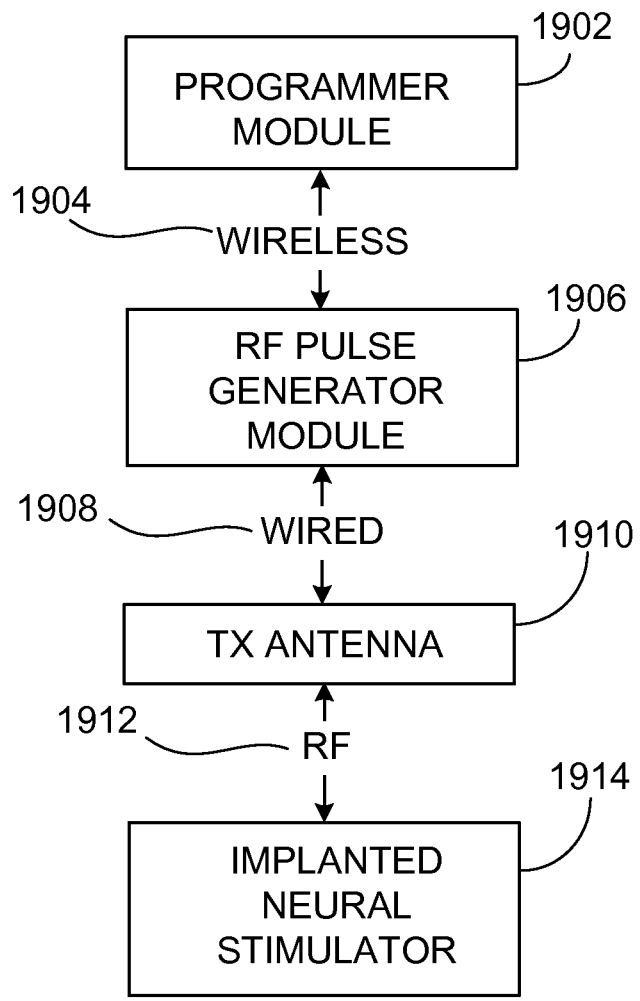
FIG. 19 depicts a high-level diagram of an example of a wireless neural stimulation system.
Figure 20:
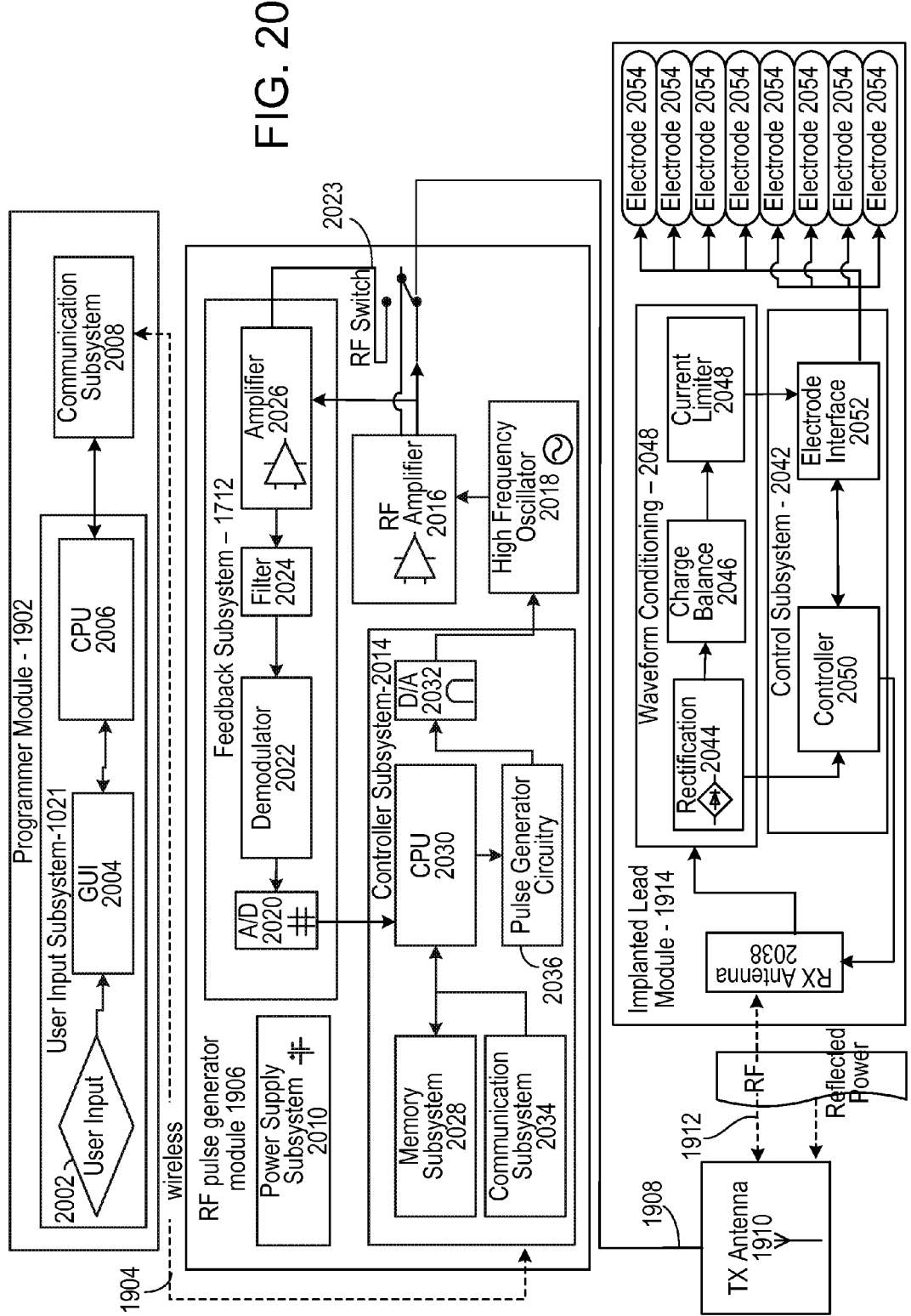
FIG. 20 depicts a detailed diagram of an example of a wireless neural stimulation system.

FIGS. 19 and 20 illustrate an example of a neural stimulation system that may employ the implantable devices described above. These implantable devices may also be referred to as implantable leads.

In particular, FIG. 19 depicts a high-level diagram of an example of a neural stimulation system. The neural stimulation system may include four major components, namely, a programmer module 1902, a RF pulse generator module 1906, a transmit (TX) antenna 1910 (for example, a patch antenna, slot antenna, or a dipole antenna), and an implanted device 1914, which may be a lead such as those described above. The programmer module 1902 may be a computer device, such as a smart phone, running a software application that supports a wireless connection 1914, such as Bluetooth®. The application can enable the user to view the system status and diagnostics, change various parameters, increase/decrease the desired stimulus amplitude of the electrode pulses, and adjust feedback sensitivity of the RF pulse generator module 1906, among other functions.

The RF pulse generator module 1906 may include communication electronics that support the wireless connection 1904, the stimulation circuitry, and the battery to power the generator electronics. In some implementations, the RF pulse generator module 1906 includes the TX antenna embedded into its packaging form factor while, in other implementations, the TX antenna is connected to the RF pulse generator module 1906 through a wired connection 1908 or a wireless connection (not shown). The TX antenna 1910 may be coupled directly to tissue to create an electric field that powers the implanted device 1914. The TX antenna 1910 communicates with the implanted device 1914 through an RF interface. For instance, the TX antenna 1910 radiates an RF transmission signal that is modulated and encoded by the RF pulse generator module 1910. The implanted device 1914 contains one or more antennas, such as dipole antenna(s), to receive and transmit through RF interface 1912. In particular, the coupling mechanism between antenna 1910 and the one or more antennas on the implanted device 1914 is electrical radiative coupling and not inductive coupling. In other words, the coupling is through an electric field rather than a magnetic field.

Through this electrical radiative coupling, the TX antenna 1910 can provide an input signal to the implanted device 1914. This input signal contains energy and may contain information encoding stimulus waveforms to be applied at the electrodes of the implanted device 1914. In some implementations, the power level of this input signal directly determines an applied amplitude (for example, power, current, or voltage) of the one or more electrical pulses created using the electrical energy contained in the input signal.

Within the implanted device 1914 are components for demodulating the RF transmission signal, and electrodes to deliver the stimulation to surrounding neuronal tissue.

The RF pulse generator module 1906 can be implanted subcutaneously, or it can be worn external to the body. When external to the body, the RF generator module 1906 can be incorporated into a belt or harness design to allow for electric radiative coupling through the skin and underlying tissue to transfer power and/or control parameters to the implanted device 1914, which can be a passive stimulator. In either event, receiver circuit(s) internal to the device 1914 can capture the energy radiated by the TX antenna 1910 and convert this energy to an electrical waveform. The receiver circuit(s) may further modify the waveform to create an electrical pulse suitable for the stimulation of neural tissue, and this pulse may be delivered to the tissue via electrode pads.

In some implementations, the RF pulse generator module 1906 can remotely control the stimulus parameters (that is, the parameters of the electrical pulses applied to the neural tissue) and monitor feedback from the wireless device 1914 based on RF signals received from the implanted wireless device 1914. A feedback detection algorithm implemented by the RF pulse generator module 1906 can monitor data sent wirelessly from the implanted wireless device 1914, including information about the energy that the implanted wireless device 1914 is receiving from the RF pulse generator and information about the stimulus waveform being delivered to the electrode pads. In order to provide an effective therapy for a given medical condition, the system can be tuned to provide the optimal amount of excitation or inhibition to the nerve fibers by electrical stimulation. A closed loop feedback control method can be used in which the output signals from the implanted wireless device 1914 are monitored and used to determine the appropriate level of neural stimulation current for maintaining effective neuronal activation, or, in some cases, the patient can manually adjust the output signals in an open loop control method.

FIG. 20 depicts a detailed diagram of an example of the neural stimulation system. As depicted, the programming module 1902 may comprise user input system 2002 and communication subsystem 2008. The user input system 2021 may allow various parameter settings to be adjusted (in some cases, in an open loop fashion) by the user in the form of instruction sets. The communication subsystem 2008 may transmit these instruction sets (and other information) via the wireless connection 1904, such as Bluetooth or Wi-Fi, to the RF pulse generator module 1906, as well as receive data from module 1906.

For instance, the programmer module 1902, which can be utilized for multiple users, such as a patient's control unit or clinician's programmer unit, can be used to send stimulation parameters to the RF pulse generator module 1906. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

TABLE 1

| Stimulation Parameter | |
|---|---|
| Pulse Amplitude: | 0 to 20 mA |
| Pulse Frequency: | 0 to 20,000 Hz |
| Pulse Width: | 0 to 2 ms |

The implantable device 1914 or RF pulse generator module 1914 (which may be a lead such as those described above) may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 1902 may be functionally a smart device and associated application. The smart device hardware may include a CPU 2006 and be used as a vehicle to handle touchscreen input on a graphical user interface (GUI) 2004, for processing and storing data.

The RF pulse generator module 1906 may be connected via wired connection 1508 to an external TX antenna 1910. Alternatively, both the antenna and the RF pulse generator are located subcutaneously (not shown).

The signals sent by RF pulse generator module 1906 to the implanted device 1914 may include both power and parameter-setting attributes in regards to stimulus waveform, amplitude, pulse width, and frequency. The RF pulse generator module 1906 can also function as a wireless receiving unit that receives feedback signals from the implanted device 1914. To that end, the RF pulse generator module 1906 may contain microelectronics or other circuitry to handle the generation of the signals transmitted to the device 1914 as well as handle feedback signals, such as those from the device 1914. For example, the RF pulse generator module 1906 may comprise controller subsystem 2014, high-frequency oscillator 2018, RF amplifier 2016, a RF switch 2023, and a feedback subsystem 2012.

The controller subsystem 2014 may include a CPU 2030 to handle data processing, a memory subsystem 2028 such as a local memory, communication subsystem 2034 to communicate with programmer module 1902 (including receiving stimulation parameters from programmer module), pulse generator circuitry 2036, and digital/analog (D/A) converters 2032.

The controller subsystem 2014 may be used by the patient and/or the clinician to control the stimulation parameter settings (for example, by controlling the parameters of the signal sent from RF pulse generator module 1906 to device 1914). These parameter settings can affect, for example, the power, current level, or shape of the one or more electrical pulses. The programming of the stimulation parameters can be performed using the programming module 1902, as described above, to set the repetition rate, pulse width, amplitude, and waveform that will be transmitted by RF energy to the receive (RX) antenna 2038, typically a dipole antenna (although other types may be used), in the wireless implanted device 2014. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 2014 may store received parameter settings in the local memory subsystem 2028, until the parameter settings are modified by new input data received from the programming module 1902. The CPU 2006 may use the parameters stored in the local memory to control the pulse generator circuitry 2036 to generate a stimulus waveform that is modulated by a high frequency oscillator 2018 in the range from 300 MHz to 8 GHz. The resulting RF signal may then be amplified by RF amplifier 2026 and then sent through an RF switch 2023 to the TX antenna 1910 to reach through depths of tissue to the RX antenna 2038.

In some implementations, the RF signal sent by TX antenna 1910 may simply be a power transmission signal used by the device 1914 to generate electric pulses. In other implementations, a telemetry signal may also be transmitted to the device 1914 to send instructions about the various operations of the device 1914. The telemetry signal may be sent by the modulation of the carrier signal (through the skin if external, or through other body tissues if the pulse generator module 1906 is implanted subcutaneously). The telemetry signal is used to modulate the carrier signal (a high frequency signal) that is coupled onto the implanted antenna(s) 2038 and does not interfere with the input received on the same lead to power the implant. In one embodiment the telemetry signal and powering signal are combined into one signal, where the RF telemetry signal is used to modulate the RF powering signal, and thus the implanted stimulator is powered directly by the received telemetry signal; separate subsystems in the stimulator harness the power contained in the signal and interpret the data content of the signal.

The RF switch 2023 may be a multipurpose device such as a dual directional coupler, which passes the relatively high amplitude, extremely short duration RF pulse to the TX antenna 1910 with minimal insertion loss while simultaneously providing two low-level outputs to feedback subsystem 2012; one output delivers a forward power signal to the feedback subsystem 2012, where the forward power signal is an attenuated version of the RF pulse sent to the TX antenna 1910, and the other output delivers a reverse power signal to a different port of the feedback subsystem 2012, where reverse power is an attenuated version of the reflected RF energy from the TX Antenna 1910.

During the on-cycle time (when an RF signal is being transmitted to the device 1914), the RF switch 2023 is set to send the forward power signal to feedback subsystem. During the off-cycle time (when an RF signal is not being transmitted to the device 1914), the RF switch 2023 can change to a receiving mode in which the reflected RF energy and/or RF signals from the device 1914 are received to be analyzed in the feedback subsystem 2012.

The feedback subsystem 2012 of the RF pulse generator module 1906 may include reception circuitry to receive and extract telemetry or other feedback signals from the device 1914 and/or reflected RF energy from the signal sent by TX antenna 1910. The feedback subsystem may include an amplifier 2026, a filter 2024, a demodulator 2022, and an A/D converter 2020.

The feedback subsystem 2012 receives the forward power signal and converts this high-frequency AC signal to a DC level that can be sampled and sent to the controller subsystem 2014. In this way the characteristics of the generated RF pulse can be compared to a reference signal within the controller subsystem 2014. If a disparity (error) exists in any parameter, the controller subsystem 2014 can adjust the output to the RF pulse generator 1906. The nature of the adjustment can be, for example, proportional to the computed error. The controller subsystem 2014 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 1910 has perfectly matched impedance to the tissue that it contacts, the electromagnetic waves generated from the RF pulse generator 1906 pass unimpeded from the TX antenna 1910 into the body tissue. However, in real-world applications a large degree of variability may exist in the body types of users, types of clothing worn, and positioning of the antenna 1910 relative to the body surface. Since the impedance of the antenna 1610 depends on the relative permittivity of the underlying tissue and any intervening materials, and also depends on the overall separation distance of the antenna from the skin, in any given application there can be an impedance mismatch at the interface of the TX antenna 1910 with the body surface. When such a mismatch occurs, the electromagnetic waves sent from the RF pulse generator 1906 are partially reflected at this interface, and this reflected energy propagates backward through the antenna feed.

The dual directional coupler RF switch 2023 may prevent the reflected RF energy propagating back into the amplifier 2026, and may attenuate this reflected RF signal and send the attenuated signal as the reverse power signal to the feedback subsystem 2012. The feedback subsystem 2012 can convert this high-frequency AC signal to a DC level that can be sampled and sent to the controller subsystem 2014. The controller subsystem 2014 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 2014 can measure the reflected-power ratio in real time, and according to preset thresholds for this measurement, the controller subsystem 2014 can modify the level of RF power generated by the RF pulse generator 1906. For example, for a moderate degree of reflected power the course of action can be for the controller subsystem 2014 to increase the amplitude of RF power sent to the TX antenna 1910, as would be needed to compensate for slightly non-optimum but acceptable TX antenna coupling to the body. For higher ratios of reflected power, the course of action can be to prevent operation of the RF pulse generator 1906 and set a fault code to indicate that the TX antenna 1910 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can lead to unwanted heating of internal components, and this fault condition means the system cannot deliver sufficient power to the implanted wireless neural stimulator and thus cannot deliver therapy to the user.

The controller 2042 of the device 1914 may transmit informational signals, such as a telemetry signal, through the antenna 2038 to communicate with the RF pulse generator module 1906 during its receive cycle. For example, the telemetry signal from the device 1914 may be coupled to the modulated signal on the dipole antenna(s) 2038, during the on and off state of the transistor circuit to enable or disable a waveform that produces the corresponding RF bursts necessary to transmit to the external (or remotely implanted) pulse generator module 1906. The antenna(s) 2038 may be connected to electrodes 2054 in contact with tissue to provide a return path for the transmitted signal. An A/D (not shown) converter can be used to transfer stored data to a serialized pattern that can be transmitted on the pulse modulated signal from the internal antenna(s) 2038 of the neural stimulator.

A telemetry signal from the implanted wireless device 1914 may include stimulus parameters such as the power or the amplitude of the current that is delivered to the tissue from the electrodes. The feedback signal can be transmitted to the RF pulse generator module 1916 to indicate the strength of the stimulus at the nerve bundle by means of coupling the signal to the implanted RX antenna 2038, which radiates the telemetry signal to the external (or remotely implanted) RF pulse generator module 1906. The feedback signal can include either or both an analog and digital telemetry pulse modulated carrier signal. Data such as stimulation pulse parameters and measured characteristics of stimulator performance can be stored in an internal memory device within the implanted device 1914, and sent on the telemetry signal. The frequency of the carrier signal may be in the range of at 300 MHz to 8 GHz.

In the feedback subsystem 2012, the telemetry signal can be down modulated using demodulator 2022 and digitized by being processed through an analog to digital (A/D) converter 2020. The digital telemetry signal may then be routed to a CPU 2030 with embedded code, with the option to reprogram, to translate the signal into a corresponding current measurement in the tissue based on the amplitude of the received signal. The CPU 2030 of the controller subsystem 2014 can compare the reported stimulus parameters to those held in local memory 2028 to verify the stimulator(s) 1914 delivered the specified stimuli to tissue. For example, if the stimulator reports a lower current than was specified, the power level from the RF pulse generator module 1906 can be increased so that the implanted neural stimulator 1914 will have more available power for stimulation. The implanted neural stimulator 1914 can generate telemetry data in real time, for example, at a rate of 8 kbits per second. All feedback data received from the implanted lead module 1914 can be logged against time and sampled to be stored for retrieval to a remote monitoring system accessible by the health care professional for trending and statistical correlations.

The sequence of remotely programmable RF signals received by the internal antenna(s) 2038 may be conditioned into waveforms that are controlled within the implantable device 1914 by the control subsystem 2042 and routed to the appropriate electrodes 2054 that are placed in proximity to the tissue to be stimulated. For instance, the RF signal transmitted from the RF pulse generator module 1906 may be received by RX antenna 2038 and processed by circuitry, such as waveform conditioning circuitry 2040, within the implanted wireless device 1914 to be converted into electrical pulses applied to the electrodes 2054 through electrode interface 2052. In some implementations, the implanted device 1914 contains between two to sixteen electrodes 2054.

The waveform conditioning circuitry 2040 may include a rectifier 2044, which rectifies the signal received by the RX antenna 2038. The rectified signal may be fed to the controller 2042 for receiving encoded instructions from the RF pulse generator module 1906. The rectifier signal may also be fed to a charge balance component 2046 that is configured to create one or more electrical pulses based such that the one or more electrical pulses result in a substantially zero net charge at the one or more electrodes (that is, the pulses are charge balanced). The charge-balanced pulses are passed through the current limiter 2048 to the electrode interface 2052, which applies the pulses to the electrodes 2054 as appropriate.

The current limiter 2048 insures the current level of the pulses applied to the electrodes 2054 is not above a threshold current level. In some implementations, an amplitude (for example, current level, voltage level, or power level) of the received RF pulse directly determines the amplitude of the stimulus. In this case, it may be particularly beneficial to include current limiter 2048 to prevent excessive current or charge being delivered through the electrodes, although current limiter 2048 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 2048 may act as a charge limiter that limits a characteristic (for example, current or duration) of the electrical pulses so that the charge per phase remains below a threshold level (typically, a safe-charge limit).

In the event the implanted wireless device 2014 receives a "strong" pulse of RF power sufficient to generate a stimulus that would exceed the predetermined safe-charge limit, the current limiter 2048 can automatically limit or "clip" the stimulus phase to maintain the total charge of the phase within the safety limit. The current limiter 2048 may be a passive current limiting component that cuts the signal to the electrodes 2054 once the safe current limit (the threshold current level) is reached. Alternatively, or additionally, the current limiter 2048 may communicate with the electrode interface 2052 to turn off all electrodes 2054 to prevent tissue damaging current levels.

A clipping event may trigger a current limiter feedback control mode. The action of clipping may cause the controller to send a threshold power data signal to the pulse generator 1906. The feedback subsystem 2012 detects the threshold power signal and demodulates the signal into data that is communicated to the controller subsystem 2014. The controller subsystem 2014 algorithms may act on this current-limiting condition by specifically reducing the RF power generated by the RF pulse generator, or cutting the power completely. In this way, the pulse generator 1906 can reduce the RF power delivered to the body if the implanted wireless neural stimulator 1914 reports is receiving excess RF power.

The controller 2050 of the device 2005 may communicate with the electrode interface 2052 to control various aspects of the electrode setup and pulses applied to the electrodes 2054. The electrode interface 2052 may act as a multiplex and control the polarity and switching of each of the electrodes 2054. For instance, in some implementations, the wireless stimulator 1906 has multiple electrodes 2054 in contact with tissue, and for a given stimulus the RF pulse generator module 1906 can arbitrarily assign one or more electrodes to 1) act as a stimulating electrode, 2) act as a return electrode, or 3) be inactive by communication of assignment sent wirelessly with the parameter instructions, which the controller 2050 uses to set electrode interface 2052 as appropriate. It may be physiologically advantageous to assign, for example, one or two electrodes as stimulating electrodes and to assign all remaining electrodes as return electrodes.

Also, in some implementations, for a given stimulus pulse, the controller 2050 may control the electrode interface 2052 to divide the current arbitrarily (or according to instructions from pulse generator module 1906) among the designated stimulating electrodes. This control over electrode assignment and current control can be advantageous because in practice the electrodes 2054 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 2050, on its own or in response to instructions from pulse generator 1906, can control electrode interface 2052 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 2050 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 2050 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 2050 was configured to match the repetition rate for set B to that of set A, for such a case the controller 2050 can specify the relative start times of the stimulus cycles to be coincident in time or to be arbitrarily offset from one another by some delay interval.

In some implementations, the controller 2050 can arbitrarily shape the stimulus waveform amplitude, and may do so in response to instructions from pulse generator 1506. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 2050 can increase or decrease the level of current at any time during the stimulus phase and/or during the charge-balancing phase. Thus, in some implementations, the controller 2050 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the device 1914 may include a charge-balancing component 2046. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units of uC/cm$^2$. In order to avoid the irreversible electrochemical reactions such as pH change, electrode dissolution as well as tissue destruction, no net charge should appear at the electrode-electrolyte interface, and it is generally acceptable to have a charge density less than 30 uC/cm$^2$. Biphasic stimulating current pulses ensure that no net charge appears at the electrode after each stimulation cycle and the electrochemical processes are balanced to prevent net de currents. The device 1914 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 2046 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment of the present invention, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless device 1914 may create a drive-waveform envelope that follows the envelope of the RF pulse received by the receiving dipole antenna(s) 2038. In this case, the RF pulse generator module 1906 can directly control the envelope of the drive waveform within the wireless device 1914, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted device 1914 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 1906, and in others this control may be administered internally by circuitry onboard the wireless device 1914, such as controller 2050. In the case of onboard control, the amplitude and timing may be specified or modified by data commands delivered from the pulse generator module 1906.

A number of implementations have been described. Nevertheless, it will be understood that various modifications may be made. Accordingly, other implementations are within the scope of the following claims.

What is claimed is:

1. A method of treating chronic pain or inflammation with neural modulation, the method comprising:

placing a surgical instrument to reach into a torso section of a patient's body, the patient suffering from chronic pain or inflammation in a primary area in the torso section;

placing a passive wireless stimulator device into an opening on the surgical instrument by placing a passive wireless stimulator device that includes one or more non-inductive antennas configured to receive electromagnetic energy radiated from a source located outside of the patient's body, electronic circuitry coupled to each of the one or more non-inductive antennas and configured to extract electric power and excitation pulses from the radiated electromagnetic energy as received by the one or more non-inductive antennas, and one or more electrodes configured to deliver the excitation pulses to the one or more excitable tissue to effectuate the neural modulation thereof, the passive wireless stimulator device suitable to fit into the opening on the surgical instrument and configured to operate without a battery or energy storage by receiving electromagnetic energy non-inductively from a source located outside the patient's body;

through the opening on the surgical instrument, positioning one or more electrodes on the passive wireless stimulator device adjacent to or near excitable tissue in the primary area in the torso section of the patient; and causing electrical pulses to be delivered to one or more electrodes on the passive wireless stimulator device such that neural modulation is applied to the excitable tissue in the primary area in the torso section.

2. The method of claim 1, wherein placing the surgical instrument comprises positioning a laparoscopic device into an abdominal region of the patient's body.

3. The method of claim 2, wherein placing a passive wireless stimulator device into an opening on the surgical instrument comprises placing the passive wireless stimulator device through a working channel or cannula of the laparoscopic device.

4. The method of claim 3, wherein positioning the passive wireless stimulator device adjacent to or near excitable tissue comprises positioning the passive wireless stimulator device adjacent to or near branches of the splenic nerve of the patient.

5. The method of claim 3, wherein positioning the passive wireless stimulator device adjacent to or near excitable tissue comprises positioning the wireless device adjacent to or near nerves within the spinal cord of the patient.

6. The method of claim 3, wherein positioning the passive wireless stimulator device adjacent to or near excitable tissue comprises positioning the passive wireless stimulator device adjacent to or near branches of the splanchnic nerve of the patient.

7. The method of claim 3, wherein positioning the passive wireless stimulator device adjacent to or near excitable tissue comprises positioning the wireless device adjacent to or near branches of the vagus nerve of the patient.

8. The method of claim 3, wherein positioning the passive wireless stimulator device adjacent to or near excitable tissue comprises positioning the wireless device adjacent to or near the celiac ganglion of the patient.

9. The method of claim 3, wherein positioning the passive wireless stimulator device adjacent to or near excitable tissue comprises positioning the passive wireless stimulator device adjacent to or near the phrenic nerve and the renal plexus of the patient.

10. The method of claim 1, wherein placing the surgical instrument comprises placing an endoscopic device into the torso section of the patient's body.

11. The method of claim 10, wherein placing a passive wireless stimulator device into an opening on the surgical instrument comprises placing the passive wireless stimulator device through a working channel or cannula of the endoscopic device.

12. The method of claim 11, wherein positioning the passive wireless stimulator device adjacent to or near excitable tissue comprises positioning the wireless device in a region in the gastro-intestinal tract or the respiratory tract of the patient.

13. The method of claim 1, wherein placing the surgical instrument comprises placing a catheter device into a thoracic region of the patient's body.

14. The method of claim 13, wherein placing a passive wireless stimulator device into an opening on the surgical instrument comprises placing the wireless device through a working channel or cannula of the catheter device.

15. The method of claim 1, wherein positioning the passive wireless stimulator device adjacent to or near excitable tissue comprises positioning the passive wireless stimulator device adjacent to or near nerves on at least one of: stomach, heart, spleen, pancreas, diaphragm, liver, or kidney of the patient.

16. The method of claim 15, wherein positioning the passive wireless stimulator device adjacent to or near excitable tissue further comprises positioning the device adjacent to or near the pancreas of the patient, and wherein causing neural modulation to be applied to the excitable tissue comprises causing sufficient neural modulation such that inflammation is reduced in the pancreas of the patient.

17. The method of claim 15 wherein causing sufficient neural modulation further comprises causing sufficient neural modulation to the TRPV1 and/or CGRP-containing neurons such that inflammation is reduced in the pancreas of the patient.

18. The method of claim 1, wherein causing neural modulation to be applied to the excitable tissue further comprises causing neural modulation of the sympathetic nervous system of the patient.

19. The method of claim 18, wherein causing neural modulation of the sympathetic nervous system of the patient comprises causing neural activation of the greater splanchnic nerve of the patient.

20. The method of claim 19, wherein causing neural modulation of the sympathetic nervous system of the patient comprises causing neural inhibition of the greater splanchnic nerve of the patient.

21. The method of claim 1, further comprising using X-Ray fluoroscopy to guide positioning the passive wireless stimulator device adjacent to or near one or more excitable tissue.

22. The method of claim 1, further comprising using ultrasound sonography to guide positioning the wireless electrode lead on the passive wireless stimulator device adjacent to or near one or more excitable tissue.

* * * * *

UNITED STATES PATENT AND TRADEMARK OFFICE
CERTIFICATE OF CORRECTION

PATENT NO. : 9,717,921 B2
APPLICATION NO. : 14/775218
DATED : August 1, 2017
INVENTOR(S) : Laura Tyler Perryman and Chad David Andresen It is certified that error appears in the above-identified patent and that said Letters Patent is hereby corrected as shown below:

On the Title Page

Column 1, Lines 1-3, item (71), delete "Laura Tyler Perryman, Miami Beach, FL (US); Chad Andresen, Miami Beach, FL (US)" and insert -- Micron Devices, LLC, Miami Beach, FL --, therefor.

In the Claims

In Claim 22, Column 34, Line 20, after "the" delete "wireless".

In Claim 22, Column 34, Line 21, after "electrode" delete "lead".

Signed and Sealed this
Sixth Day of March, 2018

Andrei Iancu
*Director of the United States Patent and Trademark Office*